United States Patent
Yang et al.

(10) Patent No.: US 11,278,259 B2
(45) Date of Patent: Mar. 22, 2022

(54) THROMBUS DETECTION DURING SCANNING

(71) Applicant: Verathon Inc., Bothell, WA (US)

(72) Inventors: Fuxing Yang, Bothell, WA (US); Joon Hwan Choi, Bothell, WA (US)

(73) Assignee: Verathon Inc., Bothell, WA (US)

( * ) Notice: Subject to any disclaimer, the term of this patent is extended or adjusted under 35 U.S.C. 154(b) by 470 days.

(21) Appl. No.: 16/264,998

(22) Filed: Feb. 1, 2019

(65) Prior Publication Data

US 2019/0261942 A1    Aug. 29, 2019

Related U.S. Application Data

(60) Provisional application No. 62/634,314, filed on Feb. 23, 2018.

(51) Int. Cl.
*A61B 8/08* (2006.01)
*G06T 7/13* (2017.01)
(Continued)

(52) U.S. Cl.
CPC ............ *A61B 8/085* (2013.01); *A61B 8/0891* (2013.01); *A61B 8/14* (2013.01); *A61B 8/463* (2013.01);
(Continued)

(58) Field of Classification Search
CPC ......... A61B 8/085; A61B 8/14; A61B 8/0891; A61B 8/5207; A61B 8/483; A61B 8/5223; A61B 8/463; G06T 7/13; G06T 7/0012; G06T 7/62; G06T 2207/20156; G06T 2207/10132; G06T 2207/30101; G16H 30/40; G06F 3/04817
See application file for complete search history.

(56) References Cited

U.S. PATENT DOCUMENTS 5,125,410 A * 6/1992 Misono ................... A61B 8/06
128/908
5,435,310 A    7/1995 Sheehan et al.
(Continued)

OTHER PUBLICATIONS

Jawaid "Segmenation of Soft atherosclerotic plaques using active contour models", City University of London, 2015 (Year: 2015).*
(Continued)

*Primary Examiner* — Colin T. Sakamoto
(74) *Attorney, Agent, or Firm* — Snyder, Clark, Lesch & Chung, LLP

(57) ABSTRACT

A system includes a probe configured to transmit ultrasound signals to a target blood vessel, and receive echo information associated with the transmitted ultrasound signals. The system may also include at least one processing device configured process the received echo information and generate an ultrasound image of the blood vessel and identify a seed position within the blood vessel based on the ultrasound image. The at least one processing device may further generate an estimated contour for a lumen of the blood vessel based on pixel intensity values associated with the ultrasound image, generate an estimated contour for the blood vessel using the pixel intensity values, determine whether a thrombus exists within the blood vessel and output image information illustrating the estimated contours of the lumen and the blood vessel.

20 Claims, 16 Drawing Sheets

(51) Int. Cl.
*G06T 7/62* (2017.01)
*A61B 8/14* (2006.01)
*G06T 7/00* (2017.01)
*A61B 8/00* (2006.01)
*G16H 30/40* (2018.01)
*G06F 3/04817* (2022.01)

(52) U.S. Cl.
CPC ............ *A61B 8/483* (2013.01); *A61B 8/5207* (2013.01); *A61B 8/5223* (2013.01); *G06T 7/0012* (2013.01); *G06T 7/13* (2017.01); *G06T 7/62* (2017.01); *G16H 30/40* (2018.01); *G06F 3/04817* (2013.01); *G06T 2207/10132* (2013.01); *G06T 2207/20156* (2013.01); *G06T 2207/30101* (2013.01)

(56) References Cited

U.S. PATENT DOCUMENTS

| | | | |
|---|---|---|---|
| 5,601,084 A | 2/1997 | Sheehan et al. | |
| 6,354,999 B1 | 3/2002 | Dgany et al. | |
| 7,233,330 B2 | 6/2007 | Moreau-Gobard et al. | |
| 7,318,804 B2 | 1/2008 | Weitzel et al. | |
| 7,611,466 B2 | 11/2009 | Chalana et al. | |
| 7,819,806 B2 | 10/2010 | Yang et al. | |
| 7,959,572 B2 | 6/2011 | Ishihara | |
| 7,970,193 B2 | 6/2011 | Rouet et al. | |
| 8,096,947 B2 | 1/2012 | Saigo et al. | |
| 8,133,181 B2 | 3/2012 | Yuk et al. | |
| 8,172,754 B2 | 5/2012 | Watanabe et al. | |
| 8,219,210 B2 | 7/2012 | Arcot-Krishnamurthy et al. | |
| 8,439,839 B2 | 5/2013 | Kadokura et al. | |
| 8,489,204 B2 | 7/2013 | Arcot-Krishnamurthy et al. | |
| 8,532,360 B2 | 9/2013 | Suri | |
| 8,556,817 B2 | 10/2013 | Naessen | |
| 8,649,582 B2 | 2/2014 | Manabe et al. | |
| 8,666,472 B2 | 3/2014 | Maltz et al. | |
| 8,852,102 B2 | 10/2014 | Miyachi | |
| 9,220,477 B2 | 12/2015 | Urabe et al. | |
| 2007/0004983 A1 | 1/2007 | Chalana et al. | |
| 2007/0036417 A1 | 2/2007 | Argiro et al. | |
| 2007/0216678 A1 | 9/2007 | Rouet et al. | |
| 2008/0033302 A1 | 2/2008 | Grady et al. | |
| 2009/0062644 A1 | 3/2009 | McMorrow et al. | |
| 2009/0204007 A1 | 8/2009 | Katoh et al. | |
| 2010/0210946 A1 | 8/2010 | Harada et al. | |
| 2010/0312090 A1 | 12/2010 | Kerwin et al. | |
| 2013/0184584 A1 | 7/2013 | Berkey | |
| 2014/0081142 A1 | 3/2014 | Toma et al. | |
| 2015/0131880 A1 | 5/2015 | Wang et al. | |
| 2020/0205750 A1* | 7/2020 | Begin | A61B 6/504 |
| 2020/0315591 A1* | 10/2020 | Perez | A61B 8/4472 |
| 2021/0090249 A1* | 3/2021 | Choi | G16H 50/20 |
| 2021/0196242 A1* | 7/2021 | Perez | A61B 8/0891 |

OTHER PUBLICATIONS

International Search Report and Written Opinion issued in corresponding International Application No. PCT/US2019/016517 dated May 9, 2019, 13 pages.

\* cited by examiner

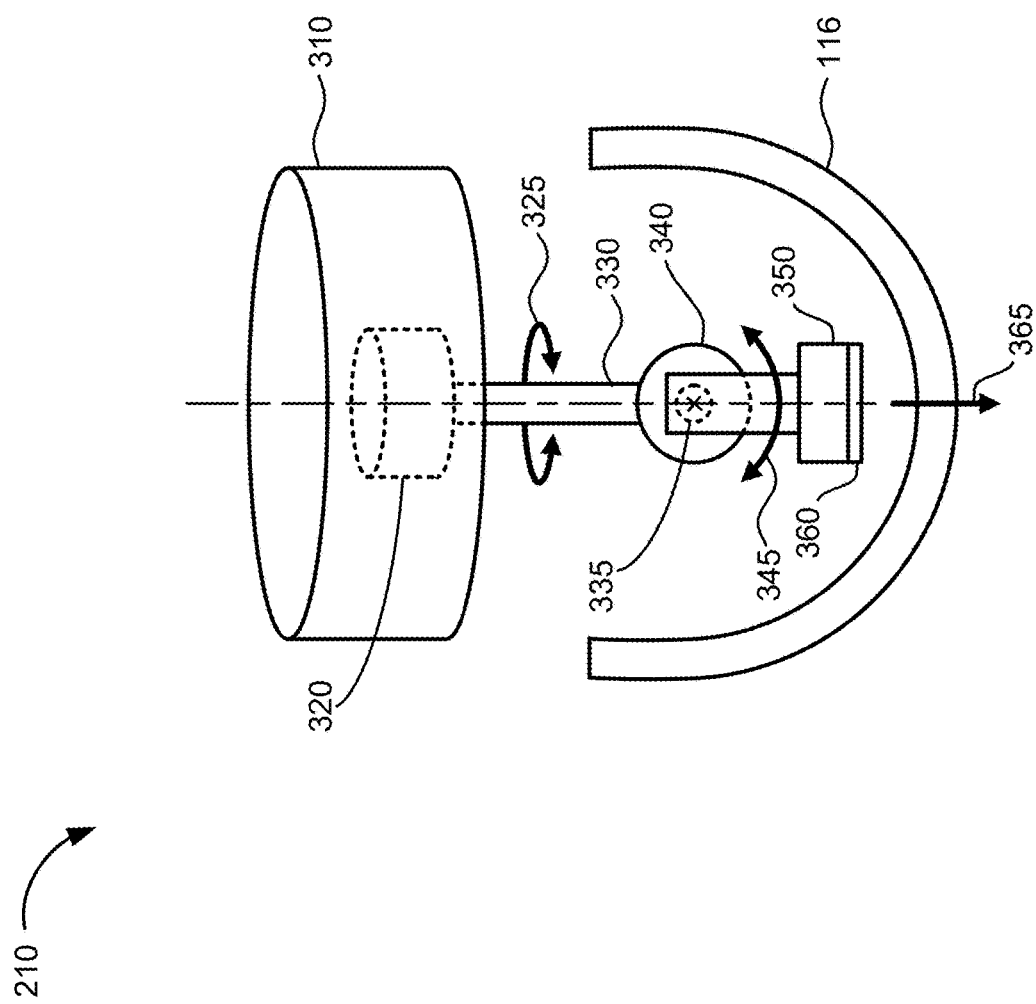

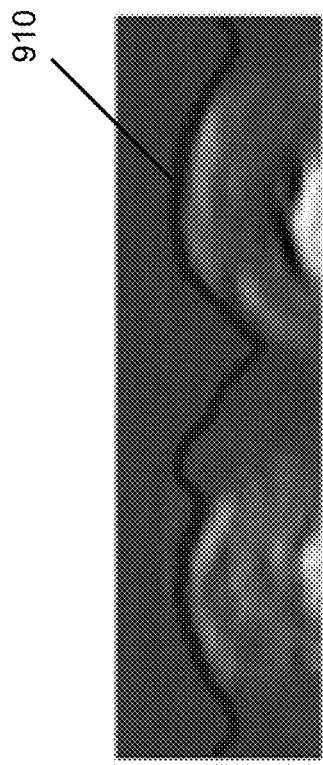 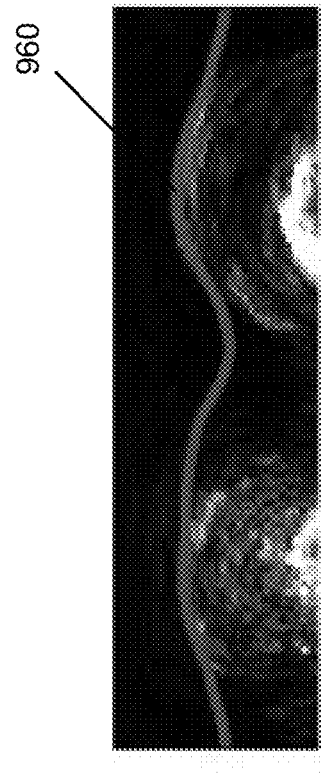
FIG. 9A
FIG. 9B

THROMBUS DETECTION DURING SCANNING

RELATED APPLICATION

This application claims priority under 35 U.S.C. § 119 based on U.S. Provisional Application No. 62/634,314 filed Feb. 23, 2018, the contents of which are hereby incorporated herein by reference in their entirety.

BACKGROUND INFORMATION

Monitoring the abdominal aorta is typically accomplished via a computed tomography (CT) scan or magnetic resonance imaging (MRI). However, imaging modalities such as CT scans, which use radiation, and MRIs are often time consuming procedures that are costly to administer. In other situations, ultrasound scanners may be used to measure features associated with the abdominal aorta.

However, monitoring/measuring features of the abdominal aorta via ultrasound is difficult due to, among other things, the possible existence of a thrombus. A thrombus is the product of blood coagulation associated with hemostasis. A thrombus may occur via the aggregation of platelets that form a platelet plug, along with the activation of the humoral coagulation system (e.g., clotting factors). A thrombus is normal in cases of injury, but is pathologic in instances of thrombosis. Ultrasound scanners often incorrectly estimate the diameter of the abdominal aorta by misinterpreting the inner rim of a thrombus located within the abdominal aorta as being part of the aorta wall. As a result, using ultrasound scanners often leads to inaccurate measurements of the true aortic diameter based on the presence of a thrombus.

In addition, a thrombus may occur based on the inappropriate activation of the hemostatic process in an uninjured or slightly injured vessel. A thrombus in a large blood vessel will decrease blood flow through that vessel, which is referred to as a mural thrombus. In a small blood vessel, the existence of a thrombus may completely cut off or block blood flow, which is referred to an occlusive thrombus. An occlusive thrombus may result in death of tissue supplied by that vessel. When a thrombus dislodges and becomes free-floating, the condition is referred to as an embolus.

Therefore, the existence of a thrombus in the abdominal aorta has many possibly adverse implications, as well as causes problems associated with monitoring features associated with the abdominal aorta. As a result, determining the existence of a thrombus and/or determining other information associated with a thrombus, such as the location of the thrombus, the size and/or area of the thrombus, etc., is useful in many situations.

BRIEF DESCRIPTION OF THE DRAWINGS

FIG. 3A illustrates a portion of the probe of FIG. 1 in accordance with an exemplary implementation;

FIGS. 9A and 9B illustrate identifying a portion of the lumen boundary in accordance with an exemplary implementation;

DETAILED DESCRIPTION OF PREFERRED EMBODIMENTS

Figure 1:
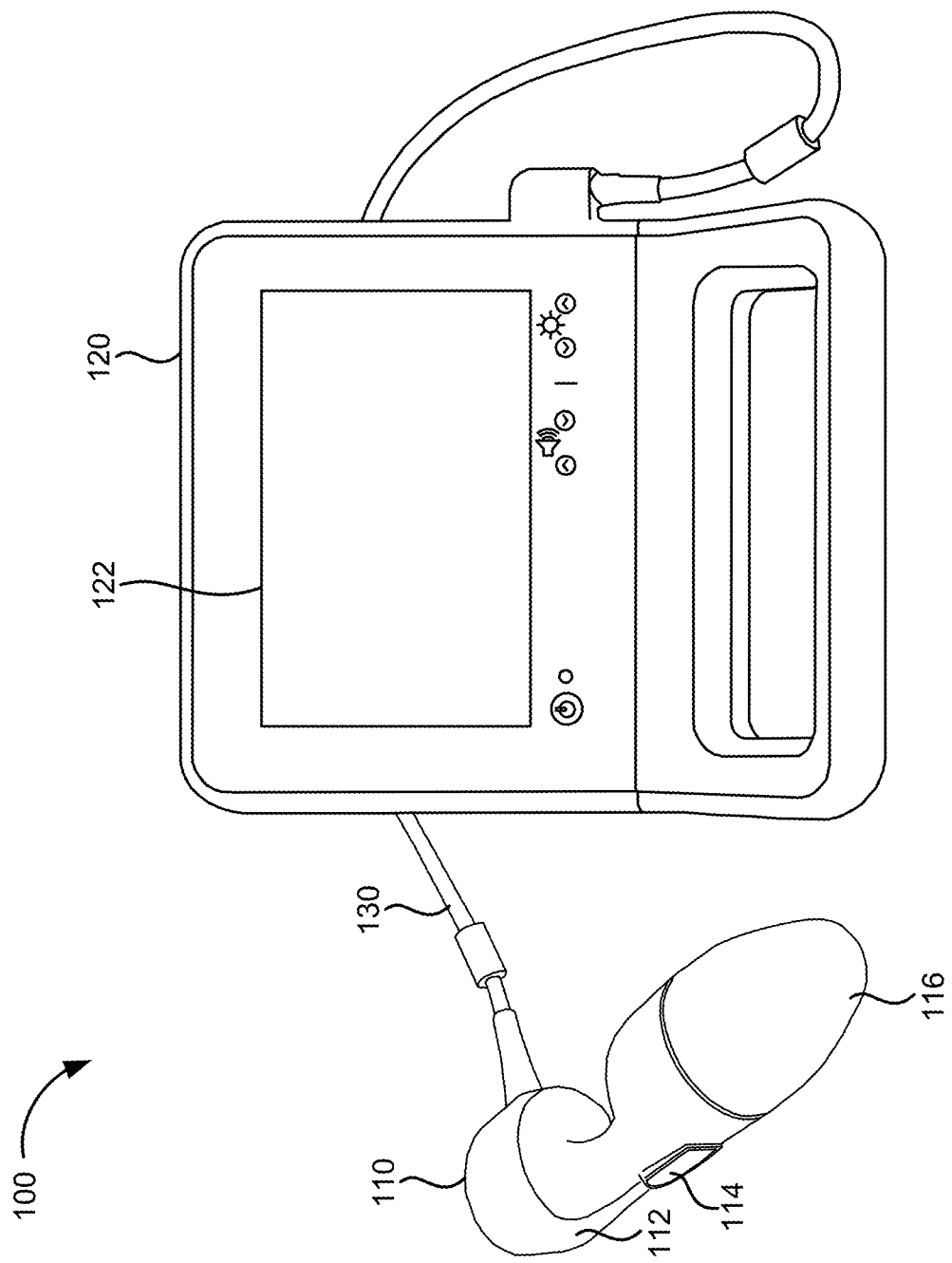
FIG. 1 illustrates an exemplary configuration of a scanning system consistent with an exemplary implementation.

The following detailed description refers to the accompanying drawings. The same reference numbers in different drawings may identify the same or similar elements. Also, the following detailed description does not limit the invention.

Implementations described herein relate to using ultrasound imaging for identifying an abdominal aorta, which may include a thrombus. The term "ultrasound image" as used herein should be broadly construed to include ultrasound images that have been pre-processed or processed. For example, pre-processing and/or processing the ultrasound images may include performing de-noising/noise reduction, image enhancement and/or segmentation, applying machine learning and/or applying other image processing techniques to ultrasound image data. In accordance with one exemplary implementation, ultrasound imaging of the abdominal aorta may be performed without the need for manual segmentation of the aorta and without using other imaging modalities, such as CT scans or MRIs. In one implementation, a lumen and/or a lumen/thrombus boundary may be identified based on brightness changes along radial profiles generated from a central portion of the lumen. The outer boundary of the aorta may also be identified based on brightness changes along radial profiles generated from the identified lumen boundary. Measurements of the aorta and determinations regarding the existence of a thrombus may then be made based on the identified boundaries.

For example, in some implementations, dynamic programming with two-dimensional (2D) or three-dimensional (3D) echo data are used to identify contours of structures of interest, such as the aorta (or other blood vessels) or other structures of interest (e.g., a thrombus) based on information obtained via an ultrasound scanner. Image segmentation may also be used to partition the image into multiple segments, such as segments that differentiate the structure of interest from surrounding tissue. In an exemplary implementation, 2D boundary detection using dynamic programming can be converted to an optimization problem seeking an optimal path in a feature map, which is based on the input image for segmentation. Optimal path searching may then be performed from one side of the image to the opposite side. In some implementations, converting a closed contour from its center (or reference contour) in Cartesian coordinates to polar coordinates may be required for closed contour detection. Dynamic programming including identifying areas of pixels having certain brightness values or ranges of brightness values may be used to estimate the boundary between various items of interest, such as a lumen boundary, the outer wall of the aorta, etc. In some implementations, machine learning, including using neural networks and deep learning, may also be used to identify the vessel, organ or structure of interest in a patient based on information obtained via an ultrasound scanner. For example, in some implementations, machine learning may be used to aid in identifying the target of interest by generating probability information associated with each portion or pixel of an image generated based on ultrasound echo data received by the ultrasound scanner.

In each case, detecting a thrombus within an aorta enables more accurate aorta wall detection and corresponding aorta measurements (e.g., diameter, area, volume, etc.). In addition, quantifying the size of the thrombus may be helpful in evaluating how severely the aorta is occluded by the thrombus. For example, complete or near complete vessel occlusion is typically associated with a high rate of mortality. Therefore, accurately identifying the thrombus and quantifying/segmenting its size can provide medical personnel with helpful information of regions where the aortic wall has abnormal thickness, which may be related to the thrombus.

FIG. 1 is a diagram illustrating an exemplary scanning system 100 consistent with an exemplary embodiment. Referring to FIG. 1, scanning system 100 includes probe 110, base unit 120 and cable 130.

Probe 110 includes handle portion 112 (also referred to as handle 112), trigger 114 and nose portion 116 (also referred to as dome or dome portion 116). Medical personnel may hold probe 110 via handle 112 and press trigger 114 to activate one or more ultrasound transceivers and transducers located in nose portion 116 to transmit ultrasound signals toward a patient's area of interest (e.g., a blood vessel, organ, joint, etc.). For example, probe 110 may be positioned over the abdominal region of a patient and over a target vessel, such as the abdominal aorta to obtain an image of the abdominal aorta.

Handle 112 allows a user to move probe 110 relative to the patient's area of interest. As discussed above, trigger 114 initiates an ultrasound scan of a selected anatomical portion while dome 116 is in contact with a surface portion of a patient's body when the patient's area of interest is scanned. Dome 116 is typically formed of a material that provides an appropriate acoustical impedance match to the anatomical portion and/or permits ultrasound energy to be properly focused as it is projected into the anatomical portion. In some implementations, an acoustic gel or gel pads may be applied to a patient's skin over the region of interest (ROI) to provide an acoustical impedance match when dome 116 is placed against the patient's skin.

Dome 116 may enclose one or more ultrasound transceiver elements and one or more transducer elements (not shown in FIG. 1). The transceiver elements transmit ultrasound energy outwardly from the dome 116, and receive acoustic reflections or echoes generated by internal structures/tissue within the anatomical portion. The one or more ultrasound transducer elements may include a one-dimensional, or a two-dimensional array of piezoelectric elements that may be moved within dome 116 by a motor to provide different scan directions with respect the transmissions of ultrasound signals by the transceiver elements. Alternatively, the transducer elements may be stationary with respect to probe 110 so that the selected anatomical region may be scanned by selectively energizing the elements in the array.

In an exemplary implementation, the scanning protocol of system 100 is configurable. For example, scanning system 100 may be configured to increase the scanning plane density, increase the scanning line numbers or change the rotational scanning to a fan scanning method to capture three-dimensional (3D) image data, depending on the particular target organ of interest, size of the target organ of interest, etc., as described in more detail below.

In some implementations, probe 110 may include a directional indicator panel (not shown in FIG. 1) that includes a number of arrows that may be illuminated for initial targeting and guiding a user to scan a vessel, organ or other structure within the ROI. For example, in some implementations, if the vessel, organ or structure is centered from placement of probe 110 placed against the dermal surface at a first location of a patient, the directional arrows may be not illuminated. However, if the vessel, organ or structure is off-center, an arrow or set of arrows may be illuminated to direct the user to reposition probe 110 at a second or subsequent dermal location of the patient. In other implementations, the directional indicators may be presented on display 122 of base unit 120.

The one or more transceivers located in probe 110 may include an inertial reference unit that includes an accelerometer and/or gyroscope positioned preferably within or adjacent to dome 116. The accelerometer may be operable to sense an acceleration of the transceiver, preferably relative to a coordinate system, while the gyroscope may be operable to sense an angular velocity of the transceiver relative to the same or another coordinate system. Accordingly, the gyroscope may be of a conventional configuration that employs dynamic elements, or may be an optoelectronic device, such as an optical ring gyroscope. In one embodiment, the accelerometer and the gyroscope may include a commonly packaged and/or solid-state device. In other embodiments, the accelerometer and/or the gyroscope may include commonly packaged micro-electromechanical system (MEMS) devices. In each case, the accelerometer and gyroscope cooperatively permit the determination of positional and/or angular changes relative to a known position that is proximate to an anatomical region of interest in the patient. Using these sensors (e.g., accelerometer, gyroscope, etc.) may help scanning system 100 reconstruct a 3D aorta vessel by combining scans at different locations, such as when the entire length of the aorta cannot be fully recovered in a single scan.

Probe 110 may communicate with base unit 120 via a wired connection, such as via cable 130. In other implementations, probe 110 may communicate with base unit 120 via a wireless connection (e.g., Bluetooth, WiFi, etc.). In each case, base unit 120 includes display 122 to allow a user to view processed results from an ultrasound scan, and/or to allow operational interaction with respect to the user during operation of probe 110. For example, display 122 may include an output display/screen, such as a liquid crystal display (LCD), light emitting diode (LED) based display, or other type of display that provides text and/or image data to a user. For example, display 122 may provide instructions for positioning probe 110 relative to the selected anatomical portion of the patient. Display 122 may also display two-dimensional or three-dimensional images of the selected anatomical region.

In some implementations, display 122 may include a graphical user interface (GUI) that allows the user to select various features associated with an ultrasound scan. For example, display 122 may include a GUI to allow a user to select whether a patient is male, female or a child. The selection of a type of patient allows system 100 to automatically adapt the transmission, reception and processing of ultrasound signals to the anatomy of a selected patient, such as adapt system 100 to accommodate various anatomical details of male, female or child patients. For example, when a child patient is selected, system 100 may be configured to adjust the transmission of ultrasound signals based on the smaller size of the child patient. In alternative implementations, system 100 may include a cavity selector configured to select a single cavity scanning mode, or a multiple cavity-scanning mode that may be used with male and/or female patients. The cavity selector may thus permit a single cavity region to be imaged, or a multiple cavity region, such as a region that includes an abdominal aorta to be imaged. In addition, the selection of the type of patient (e.g., male, female, child) may be used when analyzing the images to aid in providing an accurate representation of the target of interest. In some implementations, a training algorithm and/or machine learning may be used to reduce the processing associated with different types of patients by using sufficient clinical data/images.

To scan a selected anatomical portion of a patient, dome 116 may be positioned against a surface portion of patient that is proximate to the anatomical portion to be scanned. The user actuates the transceiver by depressing trigger 114. In response, the transducer elements optionally position the transceiver, which transmits ultrasound signals into the body, and receives corresponding return echo signals that may be at least partially processed by the transceiver to generate an ultrasound image of the selected anatomical portion. In a particular embodiment, system 100 transmits ultrasound signals in a range that extends from approximately about two megahertz (MHz) to approximately 10 or more MHz (e.g., 18 MHz).

In one embodiment, probe 110 may be coupled to a base unit 120 that is configured to generate ultrasound energy at a predetermined frequency and/or pulse repetition rate and to transfer the ultrasound energy to the transceiver. Base unit 120 also includes one or more processors or processing logic configured to process reflected ultrasound energy that is received by the transceiver to produce an image of the scanned anatomical region.

In still another particular embodiment, probe 110 may be a self-contained device that includes a microprocessor positioned within the probe 110 and software associated with the microprocessor to operably control the transceiver, and to process the reflected ultrasound energy to generate the ultrasound image. Accordingly, a display on probe 110 may be used to display the generated image and/or to view other information associated with the operation of the transceiver. For example, the information may include alphanumeric data that indicates a preferred position of the transceiver prior to performing a series of scans. In other implementations, the transceiver may be coupled to a general-purpose computer, such as a laptop or a desktop computer that includes software that at least partially controls the operation of the transceiver, and also includes software to process information transferred from the transceiver so that an image of the scanned anatomical region may be generated.

Figure 2:
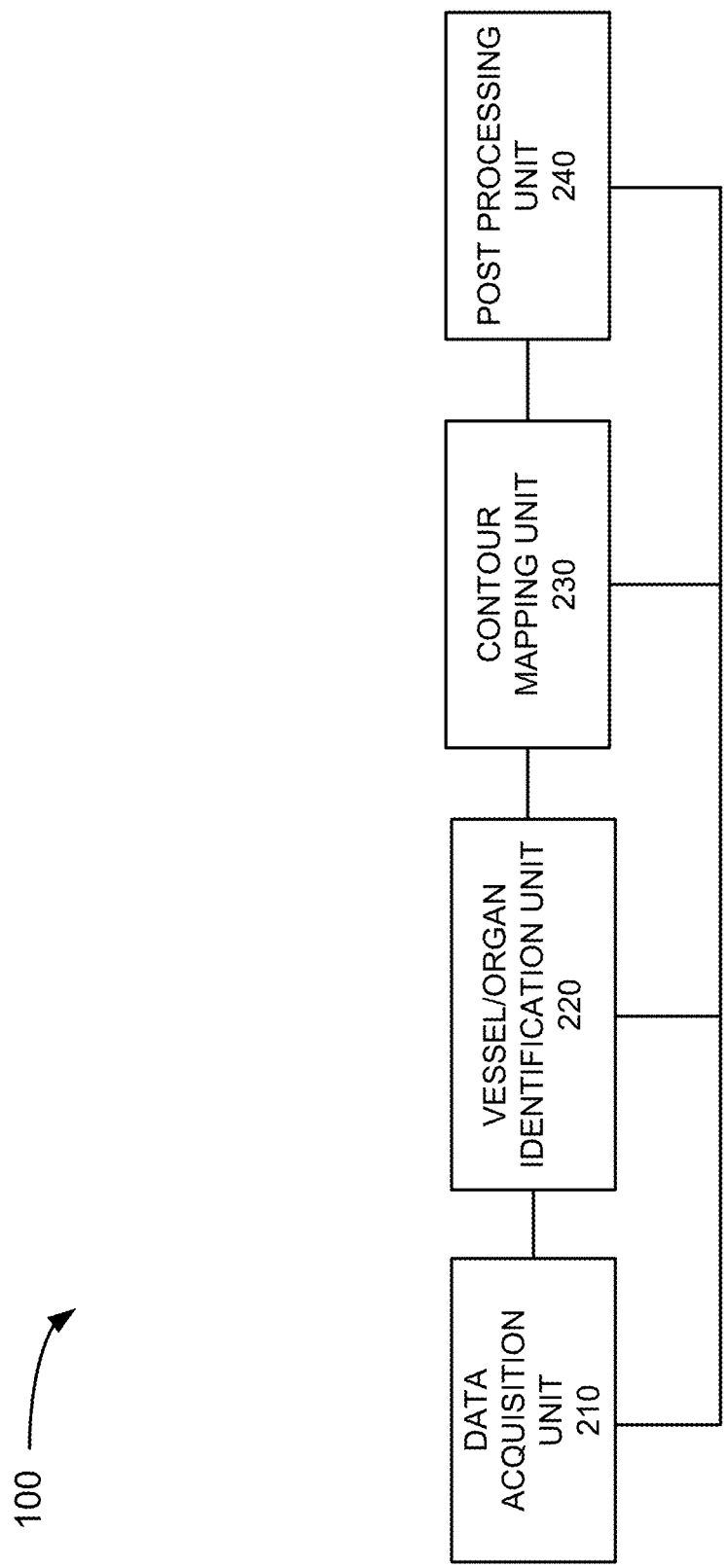
FIG. 2 illustrates an exemplary configuration of logic elements included in the scanning system of FIG. 1.

FIG. 2 is a block diagram of functional logic components implemented in system 100 in accordance with an exemplary implementation. Referring to FIG. 2, system 100 includes data acquisition unit 210, vessel/organ identification unit 220, contour mapping unit 230, and post-processing unit 240. In an exemplary implementation, data acquisition unit 210 may be part of probe 110 and the other functional units (e.g., vessel/organ identification unit 220, contour mapping unit 230, and post-processing unit 240) may be implemented in base unit 120. In other implementations, the particular units and/or logic may be implemented by other devices, such as via computing devices or servers located externally with respect to both probe 110 and base unit 120 (e.g., accessible via a wireless connection to the Internet or to a local area network within a hospital, doctor's office, etc.). For example, probe 110 may transmit echo data and/or image data to a processing system via, for example, a wireless connection (e.g., WiFi or some other wireless protocol/technology) that is located remotely from probe 110 and base unit 120.

As described above, probe 110 may include one or more transceivers that produces ultrasound signals, receives echoes from the transmitted signals and generates B-mode image data based on the received echoes. In an exemplary implementation, data acquisition unit 210 obtains data associated with multiple scan planes corresponding to the region of interest in a patient. For example, probe 110 may receive echo data that is processed by data acquisition unit 210 to generate two-dimensional (2D) B-mode image data to determine a size of the abdominal aorta and/or the size of a thrombus located in the abdominal aorta. In other implementations, probe 110 may receive echo data that is processed to generate three-dimensional (3D) image data that can be used to determine the size of the abdominal aorta.

Vessel/organ identification unit 220 may perform pre-processing of an image and detect if a vessel or organ is present within a region of interest based on, for example, differentiation of pixel intensity (e.g., as scanned and collected by data acquisition unit 210). As examples of pre-processing, vessel/organ identification unit 220 may apply noise reduction, adjust the aspect ratio of the raw B-mode image, and/or apply a scan conversion. As an example of vessel identification, in a 2D image, a blood carrying vessel may be identified as a dark region within an area of lighter-shaded pixels, where the lighter-shaded pixels typically represent body tissues.

Contour mapping unit 230 may receive data from data acquisition unit 210 and/or vessel/organ identification unit 220 and apply dynamic programming or a graphical search of the image and analyze the pixel-by-pixel data based on intensity values and/or ranges of intensity values. In one implementation, contour mapping unit 230 may apply a dynamic programming method to processes signal data sets acquired for a blood vessel (e.g., an abdominal aorta) to determine the contour along a vessel boundary, such as a vessel-tissue boundary interface, and detect the existence and/or contour of a thrombus within the vessel (e.g., an abdominal aorta thrombus, etc.).

Post processing unit 240 includes logic to identify vessel walls, such as the walls of an abdominal aorta, the walls of an abdominal aorta thrombus, etc. Post processing logic 240 may also provide "smoothing" functionality to define the walls of the vessel, thrombus, etc. Post processing logic 240 may then accurately identify a size of an abdominal aorta that includes a thrombus located in the abdominal aorta, as well as identify the size of the thrombus. For example, post processing module 240 can provide a 3D reconstruction function to fully construct the aorta structure by combining all segmentation results associated with received echo data. The aorta structure may include a lumen, a thrombus and the outer aorta walls. In this manner, the measurement of the aorta diameter will be more accurate as compared to using conventional 2D imaging, as described in detail below.

The exemplary configuration illustrated in FIG. 2 is provided for simplicity. System 100 may include more or fewer logic units/devices than illustrated in FIG. 2. For example, system 100 may include multiple data acquisition units 210 and multiple processing units that process the received data. In addition, system 100 may include additional elements, such as communication interfaces (e.g., radio frequency transceivers) that transmit and receive information via external networks to aid in analyzing ultrasound signals to identify a target in a region of interest. Furthermore, while illustrations and descriptions herein primarily refer to blood vessel applications (e.g., identifying an abdominal aorta and/or a thrombus within the abdominal aorta), other embodiments can be applied to detecting boundaries of organs, such as the bladder, prostate/kidney boundary, thyroid, etc.

FIG. 3A illustrates an exemplary data acquisition unit 210 used to obtain ultrasound image data. Referring to FIG. 3A, data acquisition unit 210 may include a single transducer element coupled to two rotational motors. In this implementation, ultrasound probe 110 may include a base 310 connected to dome 116, a theta motor 320, a spindle 330, a phi motor 340, and a transducer bucket 350 with a transducer 360. Theta motor 320, phi motor 340, transducer bucket 350 and/or transducer 360 may include wired or wireless electrical connections that electrically connect theta motor 320, phi motor 340, transducer bucket 350 and/or transducer 360 to base unit 120 via cable 130 (not shown in FIG. 3A).

Base 310 may house theta motor 320 and provide structural support to ultrasound probe 110. Base 310 may connect to dome 116 (connection not shown in FIG. 3A) and may form a seal with dome 116 to protect the components of ultrasound probe 110 from the external environment. Theta motor 320 may rotate spindle 330 with respect to base 310 in a longitudinal direction with respect to transducer 360, by rotating around a vertical axis referred to herein as a theta (θ) rotational axis 325. Spindle 330 may terminate in a shaft 335 and phi motor 340 may be mounted onto shaft 335. Phi motor 340 may rotate around an axis orthogonal to the theta rotational axis 325 around a horizontal axis referred to herein as a phi (1)) rotational axis 345. Transducer bucket 350 may be mounted to phi motor 340 and may move with phi motor 340.

Transducer 360 may be mounted to transducer bucket 350. Transducer 360 may include a piezoelectric transducer, a capacitive transducer, and/or another type of ultrasound transducer. Transducer 360, along with transceiver circuitry associated with transducer 360, may convert electrical signals to ultrasound signals at a particular ultrasound frequency or range of ultrasound frequencies, may receive reflected ultrasound signals (e.g., echoes, etc.), and may convert the received ultrasound signals to electrical signals. Transducer 360 may transmit and receive ultrasound signals in a signal direction 365 that is substantially perpendicular to the surface of transducer 360.

Signal direction 365 may be controlled by the movement of phi motor 340 and the orientation of phi motor 340 may be controlled by theta motor 320. For example, phi motor 340 may rotate back and forth across an angle that is less than 180 degrees to generate ultrasound image data for a particular plane and theta motor 320 may rotate to particular positions to obtain ultrasound image data for different planes.

In an aiming mode, theta motor 320 may remain stationary while phi motor 340 rotates back and forth to obtain ultrasound image data for a particular aiming plane. In the aiming mode, theta motor 320 may move back and forth between multiple aiming planes and phi motor 340 may rotate back and forth to obtain ultrasound image data. As an example, theta motor 320 may move between two orthogonal planes while the aiming mode is selected. As another example, theta motor 320 may sequentially rotate through three planes offset by 120 degrees to each other during the aiming mode.

Figure 3B:
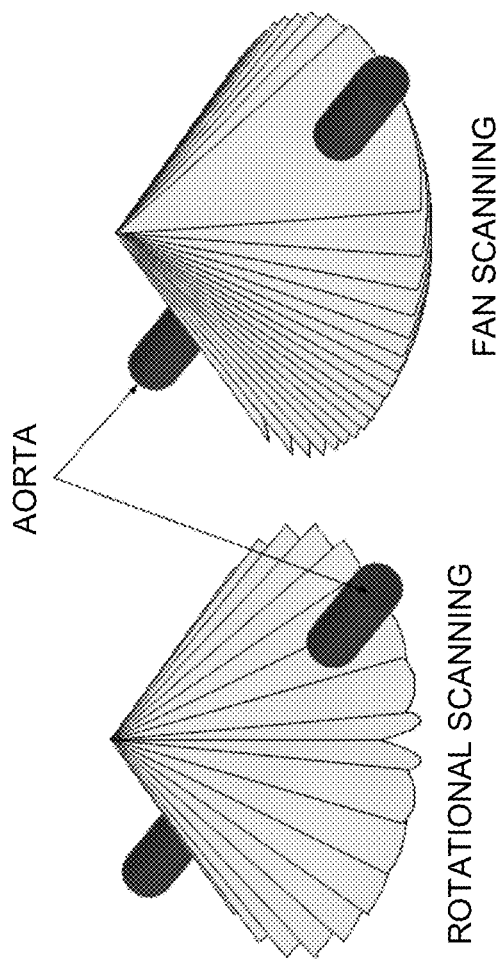
FIG. 3B illustrates capturing echo data associated with scanning planes and segmentation slices using the probe of FIG. 1.

In a 3D scan mode, theta motor 320 may cycle through a set of planes one or more times to obtain a full 3D scan of an area of interest. In each particular plane of the set of planes, phi motor 340 may rotate to obtain ultrasound image data for the particular plane. The movement of theta motor 320 and phi motor 340 may be interlaced in the 3D scan motor. For example, the movement of phi motor 340 in a first direction may be followed by a movement of theta motor 320 from a first plane to a second plane, followed by the movement of phi motor 340 in a second direction opposite to the first direction, followed by movement of theta motor 320 from the second plane to a third plane, etc. Such interlaced movement may enable ultrasound probe 110 to obtain smooth continuous volume scanning as well as improve the rate at which the scan data is obtained. In addition, theta motor 320 and phi motor 340 can be configured to increase the scanning line numbers, change the rotational scanning to a "fan scanning" method, when the entire aorta cannot be captured via a first set of scan planes and a first set of reconstructed slices, as illustrated in FIG. 3B. For example, FIG. 3B illustrates a scenario in which an initial scan did not capture the complete length of the aorta based on the length of the aorta. In this case, theta motor 320 and phi motor 340 can modify the rotational angles associated with transducer 360 to capture and evaluate vascular structures quantitatively based on cross-sectional slices to capture additional data so that the entire aorta structure can be analyzed.

Figure 4:
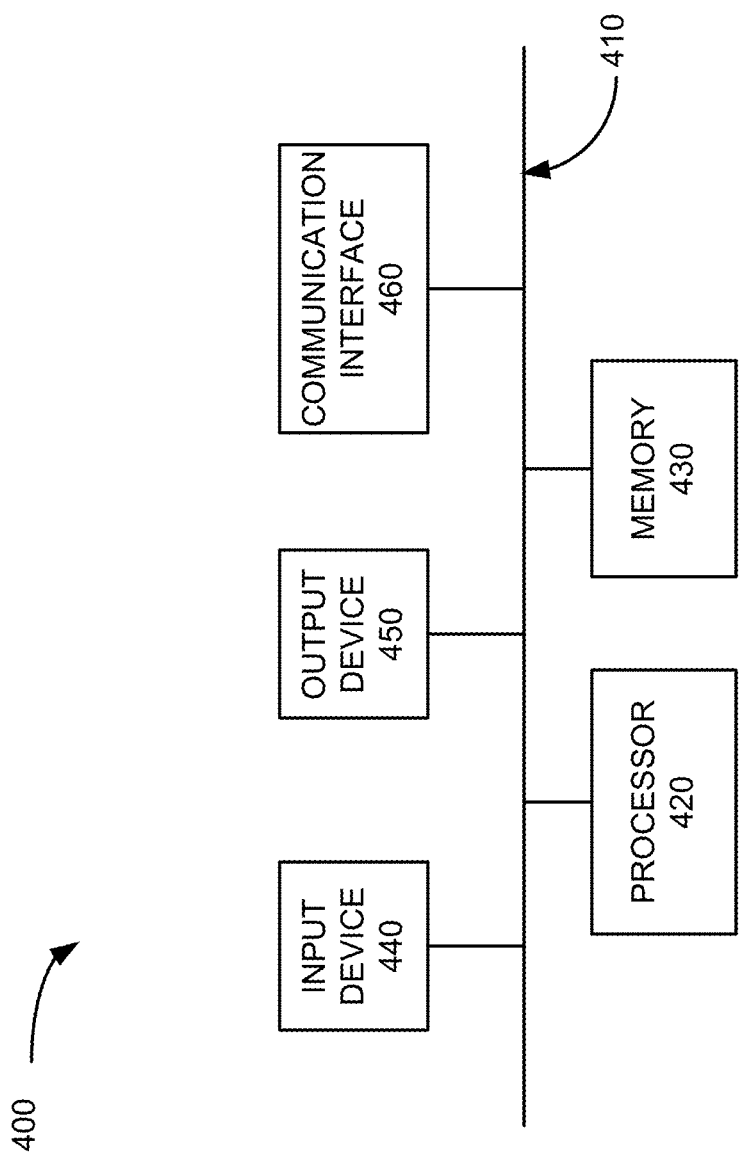
FIG. 4 illustrates an exemplary configuration of components included in one or more of the elements of FIG. 1 and/or FIG. 2.

FIG. 4 illustrates an exemplary configuration of a device 400. Device 400 may correspond to, for example, a component of data acquisition unit 210, vessel/organ identification unit 220, contour mapping unit 230 and/or post processing unit 240. Device 400 may also correspond to elements in FIG. 1, such as display 120. Referring to FIG. 4, device 400 may include bus 410, processor 420, memory 430, input device 440, output device 450 and communication interface 460. Bus 410 may include a path that permits communication among the elements of device 400.

Processor 420 may include one or more processors, microprocessors, or processing logic that may interpret and execute instructions. Memory 430 may include a random access memory (RAM) or another type of dynamic storage device that may store information and instructions for execution by processor 420. Memory 430 may also include a read only memory (ROM) device or another type of static storage device that may store static information and instructions for use by processor 420. Memory 430 may further include a solid state drive (SDD). Memory 430 may also include a magnetic and/or optical recording medium (e.g., a hard disk) and its corresponding drive.

Input device 440 may include a mechanism that permits a user to input information to device 400, such as a keyboard, a keypad, a mouse, a pen, a microphone, a touch screen, voice recognition and/or biometric mechanisms, etc. Output device 450 may include a mechanism that outputs information to the user, including a display (e.g., a liquid crystal display (LCD)), a printer, a speaker, etc. In some implementations, a touch screen display may act as both an input device and an output device.

Communication interface 460 may include one or more transceivers that device 400 uses to communicate with other devices via wired, wireless or optical mechanisms. For example, communication interface 460 may include one or more radio frequency (RF) transmitters, receivers and/or transceivers and one or more antennas for transmitting and receiving RF data via a network. Communication interface 460 may also include a modem or an Ethernet interface to a LAN or other mechanisms for communicating with elements in a network.

The exemplary configuration illustrated in FIG. 4 is provided for simplicity. It should be understood that device 400 may include more or fewer devices than illustrated in FIG. 4. In an exemplary implementation, device 400 performs operations in response to processor 420 executing sequences of instructions contained in a computer-readable medium, such as memory 430. A computer-readable medium may be defined as a physical or logical memory device. The software instructions may be read into memory 430 from another computer-readable medium (e.g., a hard disk drive (HDD), SSD, etc.), or from another device via communication interface 560. Alternatively, hard-wired circuitry, such as application specific integrated circuits (ASICs), field programmable gate arrays (FPGAs), etc., may be used in place of or in combination with software instructions to implement processes consistent with the implementations described herein. Thus, implementations described herein are not limited to any specific combination of hardware circuitry and software.

Referring again to FIG. 2, contour mapping unit 230 may receive data from data acquisition unit 210 and/or vessel/organ identification unit 220 and analyze the data on a pixel-by-pixel basis. In one implementation, contour mapping unit 230 may apply dynamic programming methods to process ultrasound signal data sets acquired for the abdominal aorta to determine the contour of the lumen of the abdominal aorta, determine whether a thrombus exists in the abdominal aorta and if so, identify a lumen-thrombus boundary, and determine the outer boundary of the aorta.

As described briefly above, in an exemplary implementation, dynamic programming and imaging segmentation may be used in connection with ultrasound scanning to estimate the size of blood vessels, organs, etc. In one implementation, 2D boundary detection associated with analyzing portions of an ultrasound image is converted into an optimization problem seeking an optimal path in a feature map (defined as F) associated with the ultrasound image. For example, a stored feature map in a 2D matrix having a size of M×N may be defined by $F \in \mathfrak{R}^{M \times N}$. The boundary detection problem with respect to various items in the feature map (e.g., a lumen, thrombus, the aorta outer wall) is then converted to an optimization problem that searches for an optimal path for the item of interest. The feature map is based on an input image which has the dimensions M×N. Assuming that searching the image proceeds from left to right, the optimization problem can be defined to find the optimal path, which is a set of row values $y_x$ across all columns from 1 to N, $\{y_x | x=1, 2, 3, \ldots N\}$, and the corresponding total cost value is globally minimized. The total cost value is defined by Equation 1 below.

$$\Sigma_{x=1}^{N} P(x, y_x);$$ Equation 1:

In an exemplary implementation, this optimization function is reformulated to implement dynamic programming with respect to an iterative cost function defined by Equation 2 below.

$$\text{Cost}(x,y) = \min_{j \in (-d,d)} \text{Cost}(x-1, y+j) + F(x,y) + \alpha|j|$$ Equation 2:

where $1 \leq x \leq N$, $1 \leq y \leq M$, $\alpha$ is a weighting parameter controlling the smoothness of the searched path and d is the maximum distance between two connected nodes in the path. Cost(x, y) is a two-dimensional cost map. In this case, the global optimization problem is the same as its sub-problem Cost(x−1, y), Cost(x−2, y), and vice versa. In one implementation, Cost(1, y)=F(1, y), is set as a boundary condition.

The optimal path or the optimal index j* can be determined by Equation 3 below.

$$j^* = \arg\min_{j \in (-d,d)} \text{Cost}(x-1, y+j) + \alpha|j|$$ Equation 3:

The index can be stored in the 2D coordinate matrix Y(x, y)=y+j*, which is a pointer indicating a point on the previous column (x−1). The cost map and path links are thus constructed column-wise from left to right on the feature matrix F. After construction, the optimal path can be found by tracing the path link backwards on the last column (x=N), which has the global minimum.

In an exemplary implementation, the feature maps from the original 2D image are based on intensity or the image brightness. For example, in a bladder ultrasound image, the bladder regions usually are much darker than the surrounding tissues, which is a key feature to help segment bladder from non-bladder region. Similarly, in an aorta ultrasound image, the lumen region is much darker than the surrounding area/tissue, which may include a thrombus that exists within the aorta.

In an exemplary implementation, ultrasound imaging can be used to screen for an Abdominal Aorta Aneurysm (AAA), also referred to as a thrombus. An AAA typically varies in size based on patient height. In general, an AAA may be defined as being greater than three centimeters (cm) in diameter at its widest point. In some instances, and in accordance with various protocols, the aorta diameter can be measured based on the lumen.

However, when a thrombus is present, conventional methods for measuring the abdominal aorta often underestimate the aorta diameter by mistaking a portion of the thrombus for the outer wall of the aorta itself. In an ultrasound image, the thrombus can cause higher echogenicity than blood inside the aorta, but the thrombus typically can cause lower echogenicity than tissues beyond the outer wall of the aorta.

Figure 5:
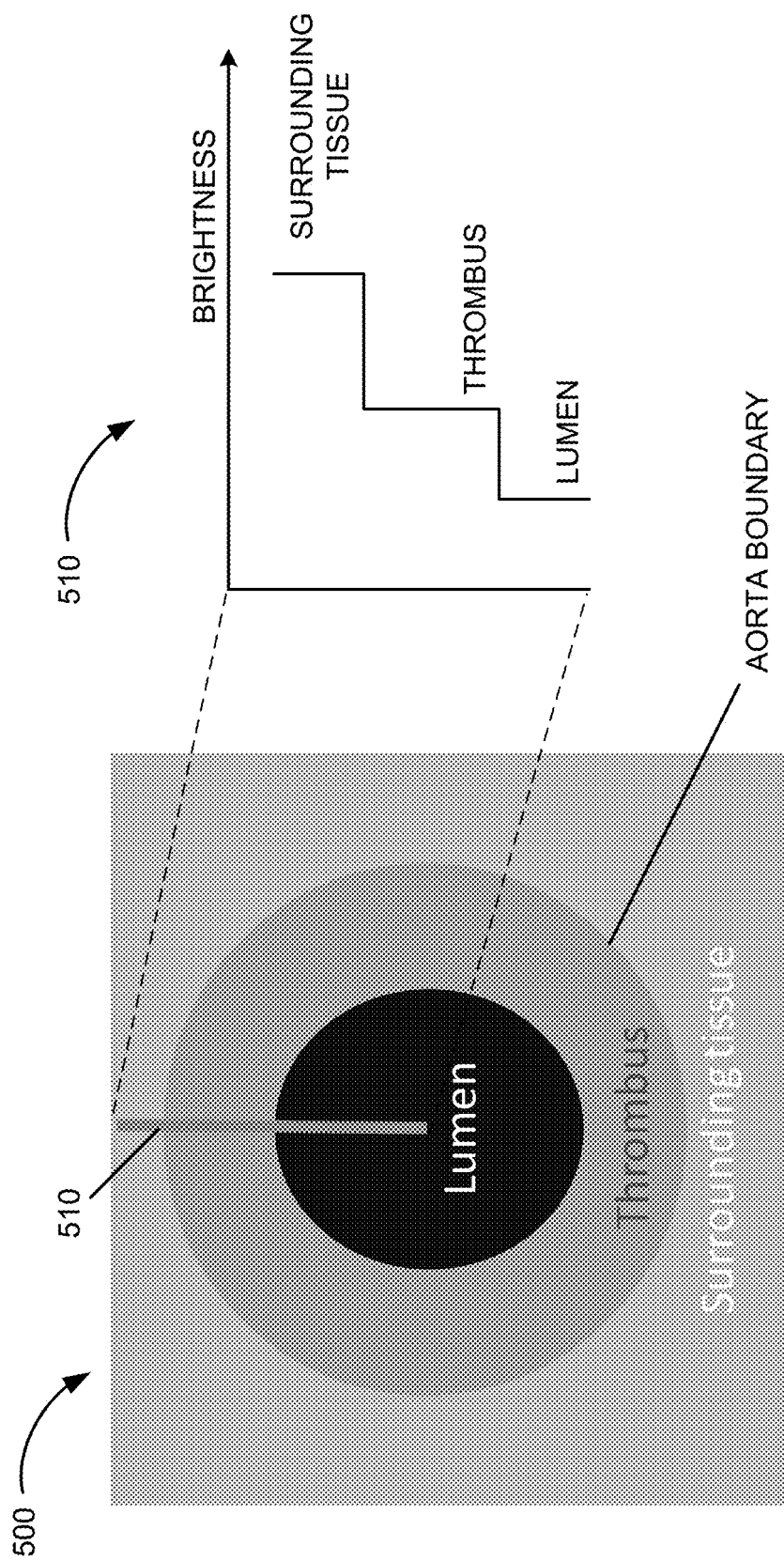
FIG. 5 is a schematic diagram illustrating a typical echo response along a radial profile for the abdominal aorta.

FIG. 5 illustrates an idealized echo response for an ultrasound image 500 along a radial profile 510 extended from the lumen. As illustrated in image 500 in FIG. 5, the lumen of the abdominal aorta is the darkest region. The tissue surrounding the aorta boundary is the brightest region, as indicated in relative brightness graph 510 shown in FIG. 5. As also indicated in FIG. 5, a thrombus may exist in the area between the lumen boundary and the aorta boundary.

In an exemplary implementation, segmentation of the lumen includes detecting the boundary of the lumen area in an ultrasound image using the expected brightness of the lumen, based on an input "seed" point. Based on the detected lumen boundary, the boundary of the aorta, which may include a thrombus, is also detected, as described in detail below.

Figure 6:
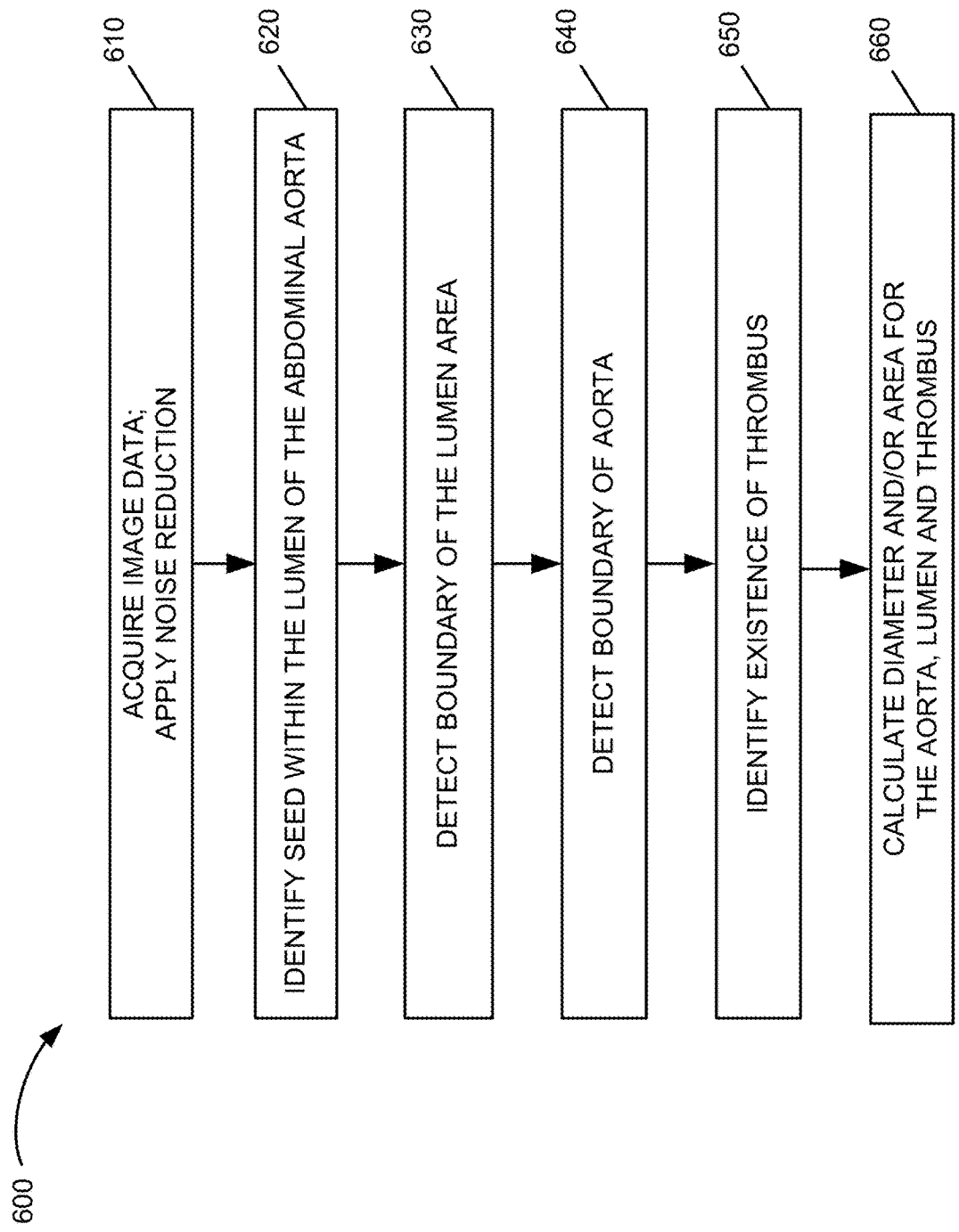
FIG. 6 is a flow diagram associated with identifying an abdominal aorta and a thrombus in accordance with an exemplary implementation.

FIG. 6 is a flow diagram illustrating exemplary processing 600 associated with identifying a target of interest, as well as identifying parameters or elements associated with the target of interest. Processing may begin with a user operating probe 110 to scan a target/region of interest. In this example, assume that the target is the abdominal aorta. It should be understood that features described herein may be used to identify other vessels, organs or structures within the body.

In an exemplary implementation, a user may press trigger 114 and the transceiver included in probe 110 transmits ultrasound signals and acquires B-mode data associated with echo signals received by probe 110 (block 610). In one implementation, data acquisition unit 210 may transmit ultrasound signals on 12 different planes through the abdominal aorta and generate 12 B-mode images corresponding to the 12 different planes. In this implementation, the data may correspond to 2D image data. In other implementations, data acquisition unit 210 may generate 3D image data. For example, as discussed above with respect to FIG. 3A, data acquisition unit 210 may perform interlaced scanning to generate 3D images to capture the entire aorta structure. In each case, the number of transmitted ultrasound signals/scan planes may vary based on the particular implementation.

Probe 110 or base unit 120 may apply a noise reduction process to the ultrasound image data (block 610). For example, data acquisition unit 210 may receive a B-mode ultrasound image from probe 110 and apply noise reduction and/or other pre-processing techniques to remove speckle and background noise from the image. In some embodiments, the aspect ratio of the raw B-mode image can be adjusted through a resizing process to compensate for differences between axial and lateral resolution. In other implementations, such as when performing an abdominal aorta scanning application, a scan conversion and/or machine learning can also be applied to make the abdominal aorta shape closer to the expected or actual shape of an abdominal aorta (e.g., elongated as opposed to round).

Figure 7A:
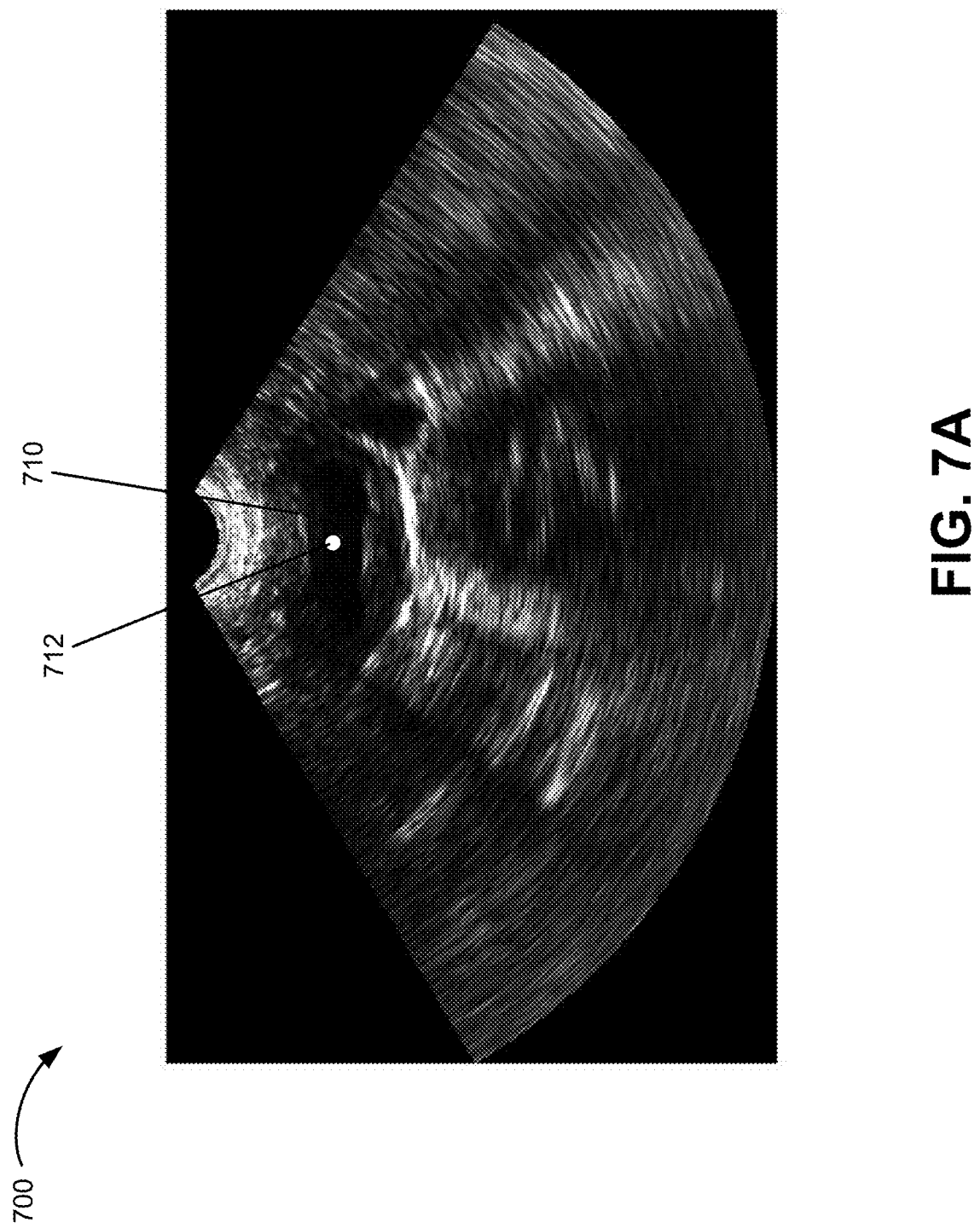
FIG. 7A illustrates selection of a seed with the lumen of an aorta in accordance with the processing of FIG. 6.

Base unit 120 (e.g., vessel/organ identification unit 220) may detect a region of interest, such as detect a concentration of dark pixels within the ultrasound image. The concentration of dark pixels typically corresponds to the lumen of the abdominal aorta, which carries the blood through the abdominal aorta. For example, FIG. 7A illustrates an image 700 that may be generated by data acquisition unit 210 and displayed via display 122 of base unit 120, which shows a concentration of dark pixels in area 710. Vessel/organ identification unit 220 may identify this area of dark pixels as the lumen. In another implementation, base unit 120 may include a user interface (e.g., a touch screen, tablet, mouse, etc.) to allow an operator to indicate or select a vessel or organ of interest, such as select the abdominal aorta lumen at area 710 via display 122.

In either case, once the abdominal aorta lumen is identified, vessel/organ identification unit 220 may identify a "seed" (also referred to as a centroid) within the lumen of the abdominal aorta (block 620). The seed may correspond to a center position or center pixel within the target vessel (e.g., the abdominal aorta, or another vessel/organ of interest) that has a darkest intensity value (e.g., lowest brightness value), where lighter or brighter areas in the image correspond to tissues or other structures having higher brightness values). For example, referring to FIG. 7A, vessel/organ identification unit 220 may identify seed 712 within lumen area 710 (depicted by an unfilled or white dot in image 700 for illustrative purposes since the actual seed 712 location within area 710 will be dark, as described above). The seed 712 may be determined manually by a human operator. Alternatively, seed 712 may be automatically generated, based on information, such as initial lumen region estimation. In either case, contour mapping unit 230 may then use seed 712 to extract profiles or other information based on the seed position.

Figure 7B:
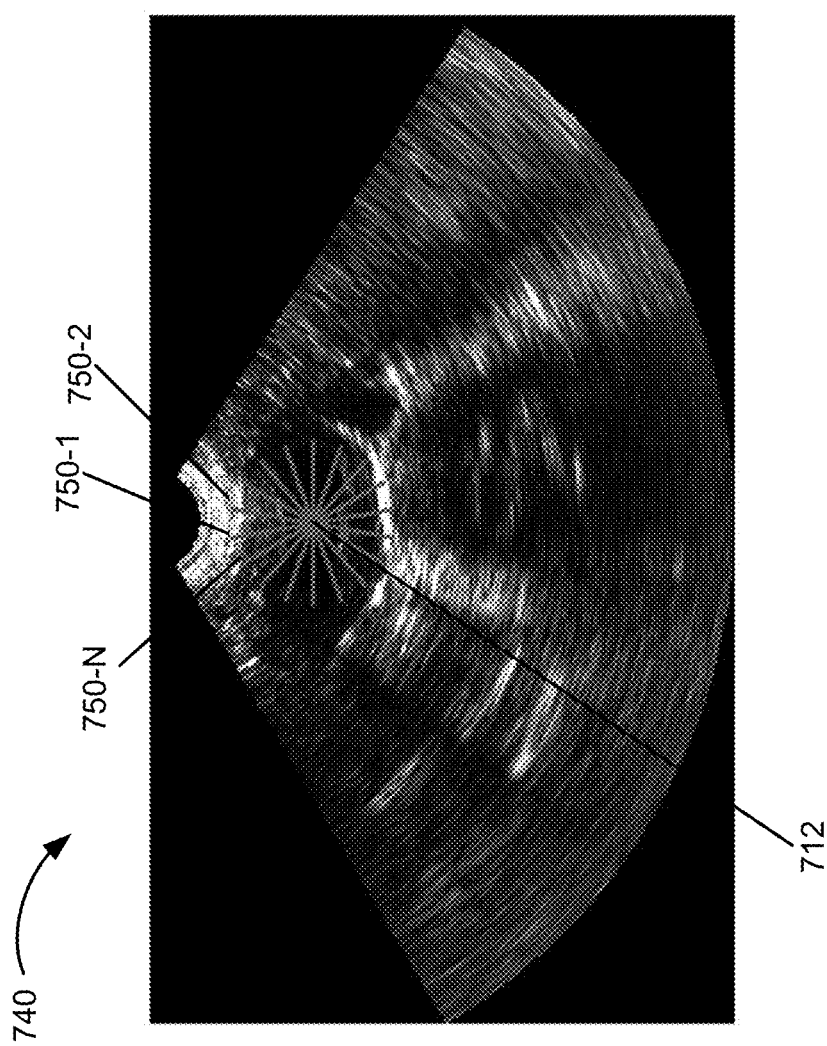
FIG. 7B illustrates the generation of radial profiles from the seed in FIG. 7A in accordance with an exemplary implementation.

For example, contour mapping unit 230 may generate radial profiles from seed 712, as illustrated in FIG. 7B. Referring to FIG. 7B, image 740 illustrates radial profiles 750-1 through 750-N extending from seed 712. Although only 18 radial profiles 750 are illustrated in FIG. 7B, in an exemplary implementation, contour mapping unit 230 may generate 180 radial profiles or lines, each separated by two radial degrees. Providing 180 radial profiles 750 increases the overall accuracy in detecting the lumen boundary. In other implementations, contour mapping unit 230 may generate more or less radial profiles. In each case, changes in brightness levels along the radial profiles 750 may be used to detect the boundary of the lumen. In an exemplary implementation in which contour mapping unit 230 generates 180 radial profiles 750 and scanning system 100 has a B-mode image resolution of approximately 0.308 millimeters/pixel, the length of radial profiles 750 is 50 pixels, M is set to 50, N is set to 180 (for the M×N feature map), and d representing a search range is set to 1.

Figure 8:
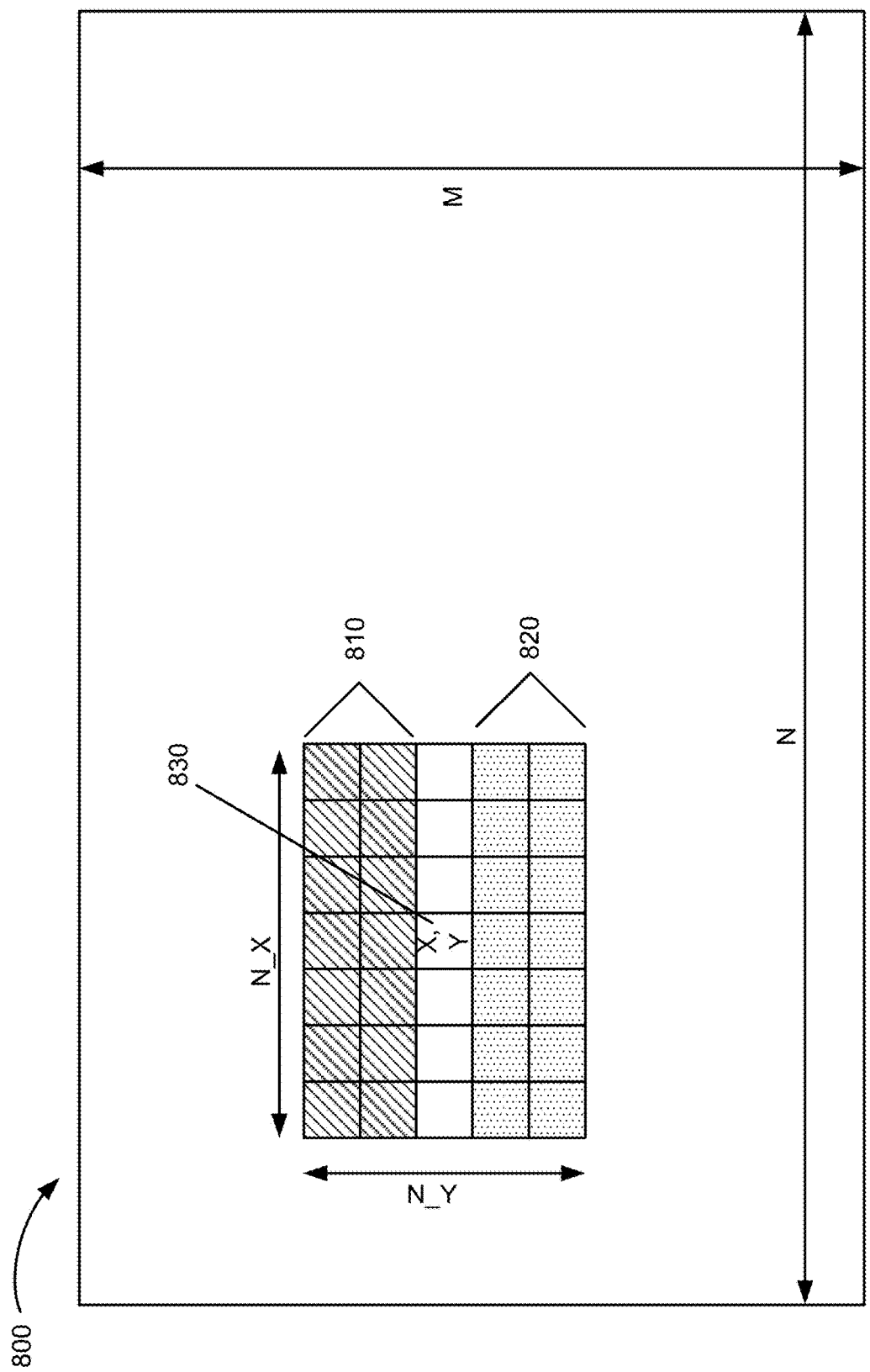
FIG. 8 illustrates a portion of a feature map in connection with detecting a lumen boundary in accordance with the processing of FIG. 6.

Contour mapping unit 230 may then detect the lumen boundary using the feature map and based on ultrasound image intensity (FIG. 6, block 630). For example, as described above with respect to FIG. 5, a thrombus and/or aorta walls can cause higher echogenicity than blood inside the aorta. As a result, pixels associated with the boundary of the thrombus and/or aorta walls typically have higher intensity values (e.g., are lighter or brighter) than pixels associated with the lumen area. FIG. 8 illustrates an exemplary feature map 800 having size of M×N, along with a portion of pixels included within feature map identified by N_X in the horizontal direction and N_Y in the vertical direction. In an exemplary implementation, the number of pixels in both the horizontal and vertical direction are odd (e.g., 1, 3, 5, 7, . . . ) to facilitate identifying a boundary between lighter and darker pixels. Referring to FIG. 8, contour mapping unit 230 may calculate the gradient G as the difference of the average intensity in the upper region of pixels shown via cross-hatching (labeled 810) and the average intensity in the lower region of pixels shown via dotted pattern (labeled 820) at every (X,Y) location inside feature map 800. When contour mapping unit 230 determines that the difference is small, it is more likely that the (X,Y) point labeled 830 in FIG. 8 is at the location/interface between the lumen and a thrombus. That is, (X,Y) point 830 is part of the lumen boundary.

In an exemplary implementation, contour mapping unit 230 may store a number of rules with respect to lumen boundary detection. For example, contour mapping unit 230 may set a penalty (P_d) based on the distance from seed 712. For example, the further away the location of a potential boundary point or candidate node of the boundary is from seed 712, the larger the penalty value. For example, contour mapping unit 230 may set the penalty based on Y/radius, where Y represents the distance of a candidate node/pixel or portion of the boundary from seed 712 and the radius represents the length of radial profile 750. Contour mapping unit 230 may also set a penalty P_A based on the intensity of data within the feature map. For example, contour mapping unit 230 may increase the penalty P_A for an (X,Y) location/candidate node in the potential boundary when the brightness of that (X,Y) location is higher/brighter than an expected intensity value since the boundary for the lumen is likely located at a less bright or shallower location.

In one implementation, contour mapping unit 230 may use the stored rules and generate the full feature calculation based on equation 4 below.

$$F(X,Y)=G+a\times P\_d+b\times P\_A, \text{ where } N\_X=7, N\_Y=7, a=1.5 \text{ and } b=1.0,\quad\text{Equation 4:}$$

where G represents the gradient defined based on the differences in average intensity of some pixels with respect to adjacent pixels described above with respect to FIG. 8. Contour mapping unit 230 may perform dynamic programming on the feature map F(X,Y) to search for the path with the minimum cost. In one implementation, contour mapping unit may set $\alpha=0.25$ in Equations 2 and 3 above to control the smoothness during searching. In addition, extra smoothing may be applied after the path is found by using a moving average window having a particular size, such as 10 pixels in size. FIG. 9A illustrates an image 900 corresponding to a portion of an optimal path 910 of the lumen boundary based on the Cost defined in Equation 2 above. FIG. 9B illustrates an image 950 corresponding to a portion of optimal path 960, which is a smoothed version of path 910 in FIG. 9A. As illustrated, contour mapping unit 230 and/or post processing unit 240 smooth the contour in accordance with various averaging and/or using information associated with expected lumen shapes. For example, the expected lumen boundary will not include sharp corners or angles. Therefore, in an exemplary implementation, contour mapping unit 230 and/or post processing unit 240 may determine first cost values based on the pixel values (e.g., intensity values) at or around candidate nodes, and then generate second cost values that correspond to or describe the local smoothness of the contour based on the candidate node positions. Contour mapping unit 230 and/or post processing unit 240 may then select the final contour of the lumen (or abdominal aorta) that minimizes the global weighted sum of the first and second cost values.

Figure 10:
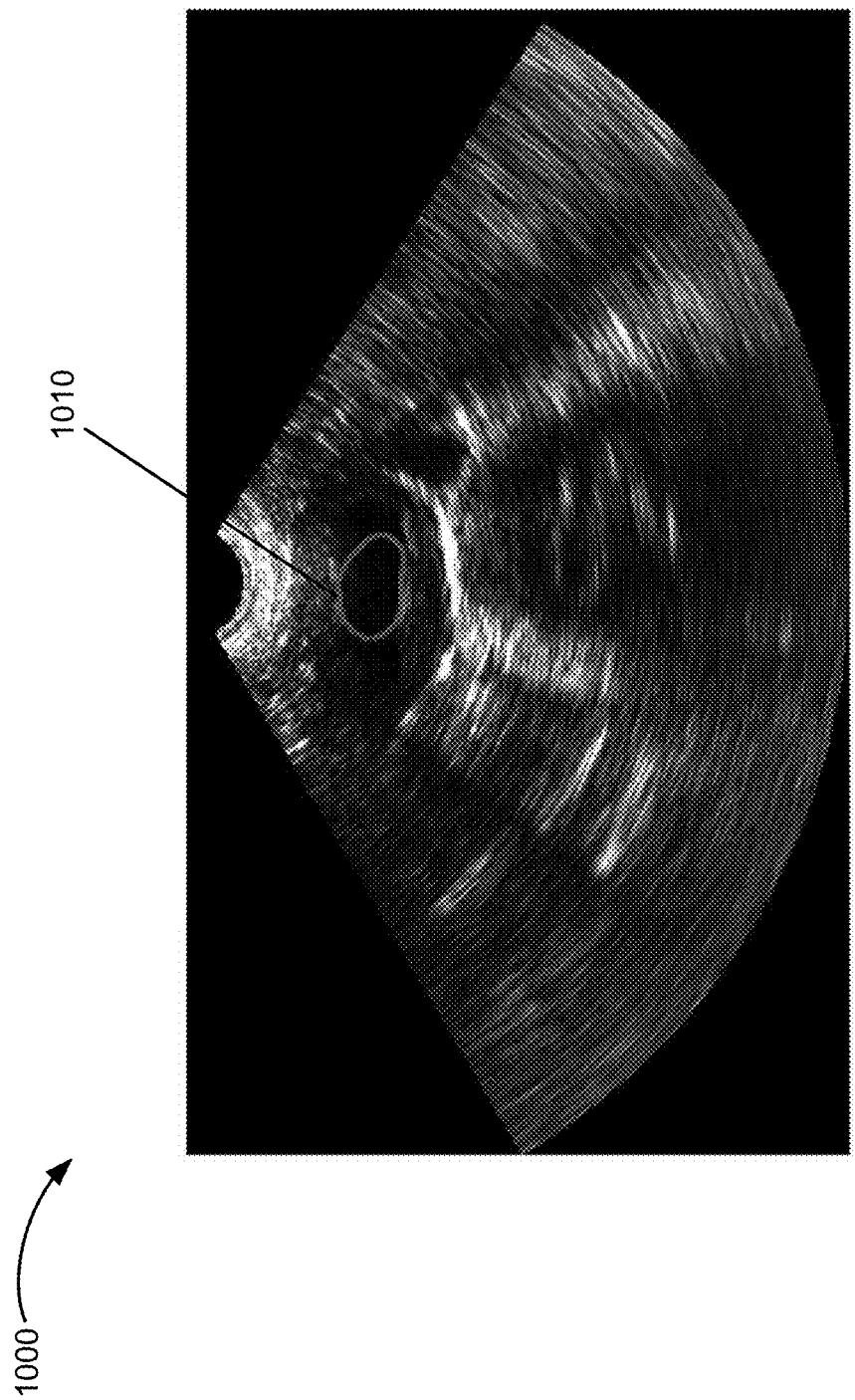
FIG. 10 is a diagram illustrating a graphical representation of the lumen boundary in accordance with an exemplary implementation.

Contour mapping unit 230 may then convert the optimal smoothed path in polar coordinates to Cartesian coordinates to define the lumen boundary for output via, for example, display 122, as illustrated in FIG. 10. For example, referring to FIG. 10, image 1000 includes a boundary 1010 that defines the boundary of the lumen.

Figure 11:
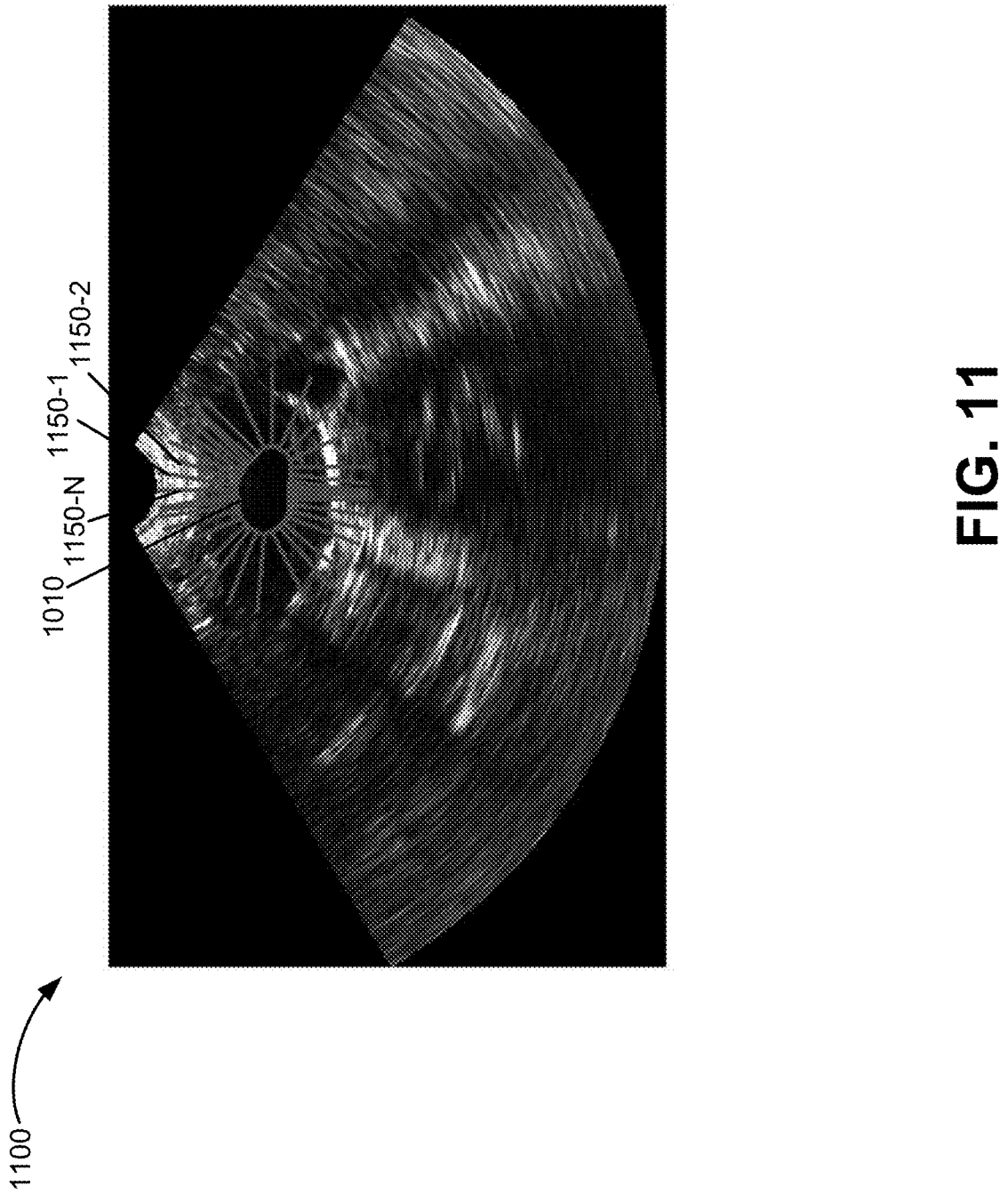
FIG. 11 illustrates the generation of radial profiles from the lumen boundary of FIG. 10 in accordance with an exemplary implementation.
Figure 12:
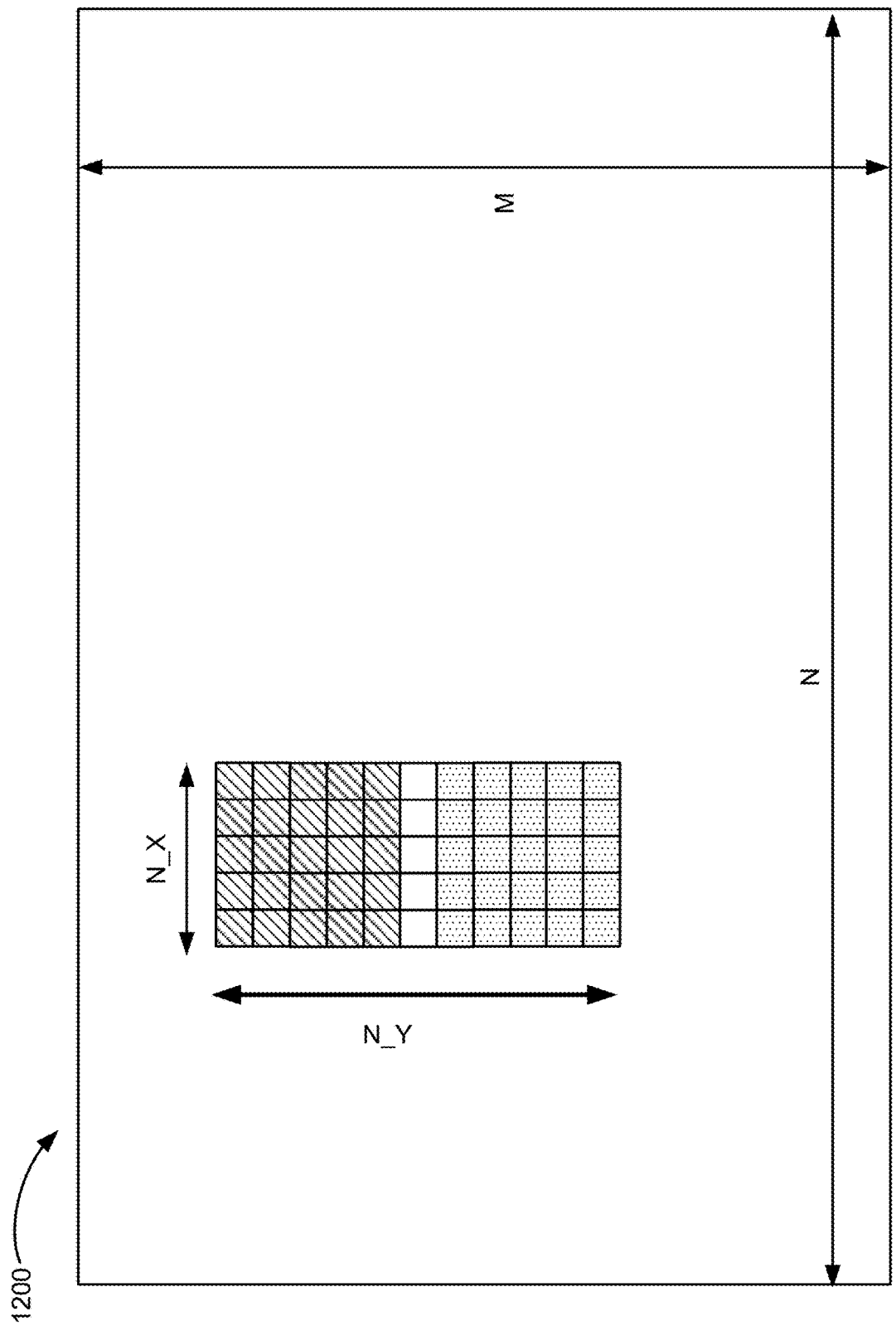
FIG. 12 illustrates a portion of a feature map in connection with detecting a thrombus and/or aorta boundary in accordance with the processing of FIG. 6.

After the lumen boundary is detected, contour mapping unit 230 may use the feature map based on ultrasound image intensity to detect the boundary of the aorta (block 640). For example, in an exemplary implementation, contour mapping unit 230 may use the detected lumen boundary and extract a new set of radial profiles along the lumen boundary. For example, FIG. 11 illustrates radial profiles 1150-1 through 1150-N extended from lumen boundary 1010 from FIG. 10. In an exemplary implementation, the radial profiles 1150 have the same length as the lumen boundary and the height is set at 50 pixels. Contour mapping unit 230 may use the feature map based on ultrasound image intensity and determine the gradient G within the feature map along the radial profiles 1150, similar to that described above with respect to radial profiles 750 for the lumen boundary. However, for the thrombus detection, N_X and N_Y configuration/size may be different. For example, in one implementation, contour mapping unit 230 may set N_X to 5 and N_Y to 11, as illustrated in a portion of feature map 1200 in FIG. 12. In FIG. 12, the average intensity in the upper region of pixels is shown via cross-hatching and the average intensity in the lower region of pixels is show via a dotted pattern.

Figure 13:
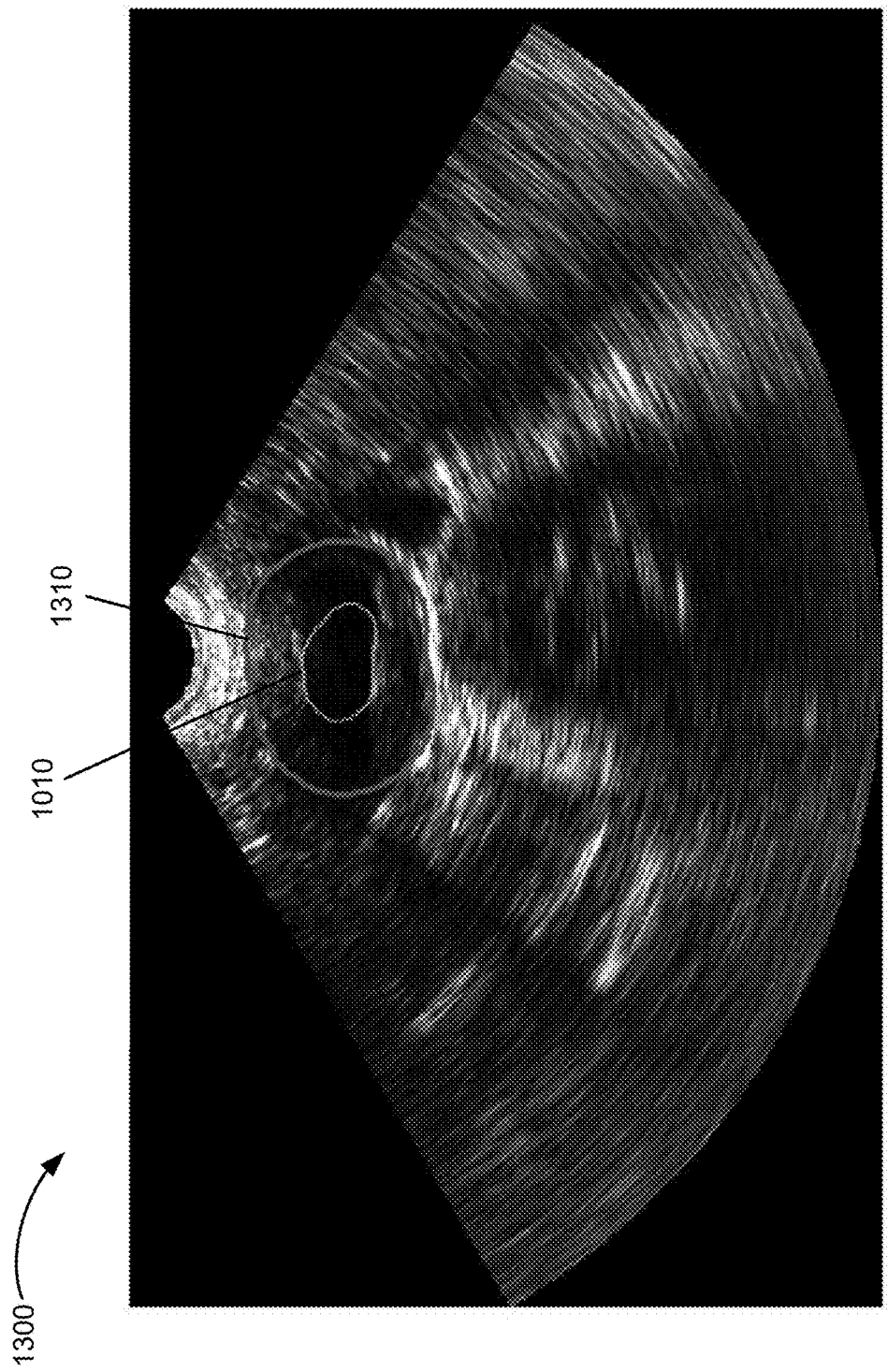
FIG. 13 is a diagram illustrating a graphical representation of the lumen and aorta boundaries in accordance with an exemplary implementation.

Similar to the discussion above with respect to the lumen detection, contour mapping unit 230 may perform dynamic programming on the feature map to search for the path/candidate nodes with the minimum cost. In one implementation, contour mapping unit 230 may set $\alpha=0.2$ in Equations 2 and 3 above to control the smoothness during searching. Contour mapping unit 230 may apply additional smoothing after the path is found by using a moving average window having a particular size, such as 10 pixels in size, to generate a contour for the boundary of the aorta (block 640). For example, referring to FIG. 13, contour mapping unit 230 may convert the optimal path based on the costs along radial profiles 1150 in polar coordinates to Cartesian coordinates to generate the aorta boundary 1310. As illustrated in FIG. 13, the distance or thickness between the lumen boundary 1010 and the aorta boundary 1310 is relatively large, indicating that a thrombus exists within the area between the lumen and outer aorta walls, as described in more detail below.

Vessel/organ identification unit 220 and/or contour mapping unit 230 may then identify whether a thrombus exists within the abdominal aorta (block 650). For example, as described above with respect to FIG. 5, a thrombus may have higher echogenicity than blood inside the aorta, but lower echogenicity than tissue surrounding the outer wall of the aorta. Contour mapping unit 230 may use this information to determine whether areas of brighter pixels exist near the lumen, as well as determine whether even brighter pixels exist further away from the lumen, which may correspond to a thrombus. In typical situations, if no thrombus exists, the lumen boundary (e.g., boundary 1010) will typically be located close to the outer aorta boundary (boundary 1310).

In typical scenarios, if a thrombus exists, the thrombus will typically be located between the lumen boundary and aorta boundary, as indicated in FIG. 5, such as where the distance or thickness between the lumen boundary and aorta boundary is unusually large. In an exemplary implementation, contour mapping 230 and/or post processing unit 240 may identify the existence of a thrombus based on the distance or thickness between the lumen boundary and the aorta boundary, such as the distance/thickness being greater than some value. In other implementations, contour mapping unit 230 and/or post processing unit 240 may identify the existence of a thrombus based on the size and/or area of the lumen compared with the size and/or area of the entire aorta. For example, if the size/area of the lumen is relatively small with respect to the size/area of the aorta, such as the area of the lumen is less than a predetermined percentage of the area of the aorta (e.g., less than 60%, 75% or some other percentage), contour mapping unit 230 and/or post processing unit 240 may determine that a thrombus exists.

For example, referring to the example in FIG. 13 and image 1300, the distance or thickness between lumen boundary 1010 and aorta boundary 1310 is relatively large and the size/area of the lumen (e.g., diameter of the lumen) with respect to the size/area of the aorta (e.g., diameter of the aorta) is relatively small. In this case, vessel/organ identification unit 220 and/or post processing unit 240 may identify that a thrombus exists (block 650). In some implementations, contour mapping unit 230 may map and/or provide a visual indicator regarding the thrombus. For example, using brightness levels as described above with respect to FIG. 5, contour mapping unit 230 may identify the contour of the thrombus. In other implementations, contour mapping unit 230 may visualize the thrombus region by highlighting the area with a different color than the lumen, providing an arrow and/or text identifying the thrombus region or providing another visual indicator regarding the existence and/or location of the thrombus.

Post processing unit 240 may then determine the diameter and/or the size/area of the aorta, and the diameter and/or the size/area of the lumen (block 660). For example, post processing unit 240 may determine size information for both the aorta and lumen, such as the diameter of the aorta, the total area of the aorta, the diameter of the lumen, the total area of the lumen. In some implementations, post processing unit 240 may also estimate the size/area of the thrombus, or thrombus region, such as the diameter of thickness of the thrombus or thrombus region. Since the thrombus is not a tubular structure, the total area of the thrombus and/or the ratio of the thrombus region to the overall aorta or aneurysm area may be a useful quantitative measure. To accurately measure the aorta diameter, probe 110 or the scanning plane needs to be perpendicular to the aorta. Otherwise, falsely high values may result. Therefore, in this example (and in FIG. 14), it is assumed the scanning plane is perpendicular to the aorta.

In each case, post processing unit 240 may output the size and/or area information via, for example, display 122 or via a display on probe 110. The size or total area of the thrombus region may correspond to the area between lumen boundary 1010 and aorta boundary 1310. That is, the area between the lumen and outer aorta wall may correspond to the area in which a thrombus exists. In this manner, scanning system 100 correctly identifies lumen boundary 1010 and aorta boundary 1310, as opposed to mistakenly identifying the thrombus or part of the thrombus as being the outer wall of the aorta, thereby avoiding errors associated with estimating the size/area of the aorta. In some implementations, contour 1010 is illustrated in a different color then contour 1310 to provide the operator of system 100 with an easy to understand visual depiction of the lumen and aorta outer wall. In still other implementations, the area in which a thrombus exists may be provided in a different color than the lumen area, be labeled with text and/or an arrow indicating a thrombus region, or provided with some other indicator to represent the existence of a thrombus.

Figure 14:
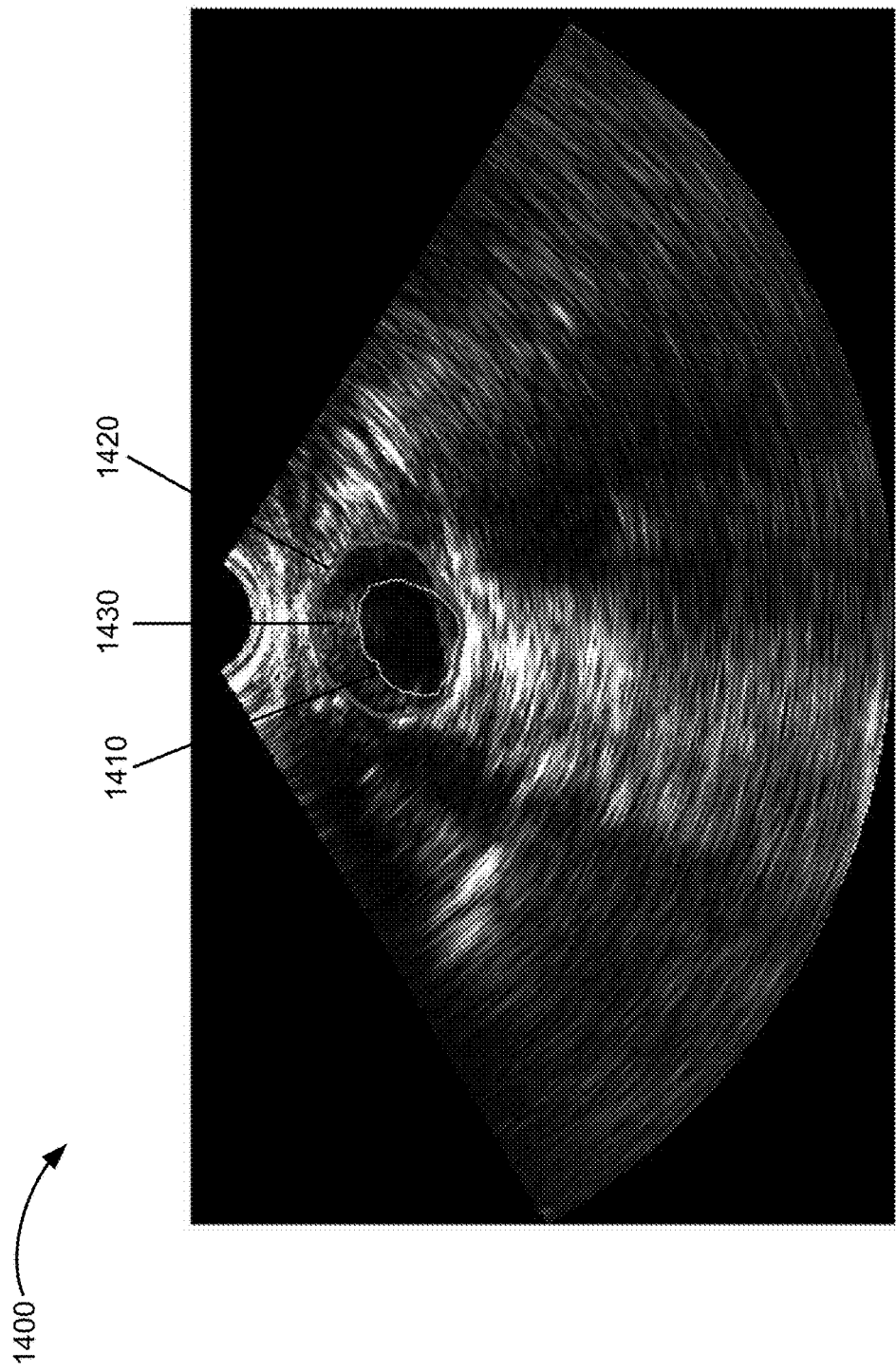
FIG. 14 is a diagram illustrating a graphical representation of the lumen and aorta boundaries in accordance with another exemplary implementation.

FIG. 14 illustrates another exemplary image 1400 that includes a lumen identified by contour 1410 and the outer aorta wall, identified by contour 1420. In this example, the lumen 1410 in not centrally located within the aorta, but is located more in the lower area (in the vertical direction) of the aorta. The diameter of the abdominal aorta and lumen may then be measured based on image 1400 and output via display 122 or another display. Again, in some implementations, contour 1410 may be provided in a different color (e.g., yellow) than contour 1420 (e.g., red). In this example, post-processing unit 240 may identify the existence of a thrombus between the upper portion of the lumen boundary 1410 and aorta contour 1420 at location 1430, as illustrated in FIG. 14. As described above, in some implementations, post processing unit 240 may provide an indicator, such as an arrow, text and/or a different color at location 1430 to indicate the location of a thrombus to aid medical personnel in the diagnosis of the thrombus.

As described above, system 100 may use dynamic programming to identify a thrombus with an abdominal aorta, as well as the outer aorta wall. In each case, system 100 may identify an area near the lumen that is lighter or brighter in intensity than lumen area, but is not as bright in intensity as surrounding tissue. This lighter area may correspond to a thrombus layer located inside the abdominal aorta. In such a case, contour mapping unit 230 may determine that a thrombus is located in the abdominal aorta. If contour mapping unit 230 does not detect an area of lighter pixels that is located in an area/region in which a thrombus may occur, contour mapping unit 230 and/or post processing unit 240 may determine that no thrombus exists. In other implementations, if the size/area of the lumen is relatively large when compared to the size/area of the aorta, post processing unit 240 may determine that no thrombus exists. In this case, the location of the lumen boundary may be very close to the boundary of the outer aorta wall.

Implementations described herein refer to processing ultrasound images using brightness differences/levels to identify various vessels and/or structures, such as a lumen, thrombus and aorta. As described above, in some implementations, the lumen may be darker than the thrombus, which may be darker than surrounding tissues. However, in other implementations and based on pre-processing of images, the thrombus may not be significantly brighter than the lumen area. Further, pre-processing output of ultrasound images may be multi-channel, such as output with pixels having red-green-blue (RGB) colors/color values or a stack of multiple images having different colors and/or intensities. In such implementations, various pixel values associated with portions of images may be used to detect the item of interest, such as the thrombus, as opposed to brightness values. In addition, the multiple images may include information from other modalities, such as color and/or pulsed wave (PW) Doppler and harmonic mode imaging.

Implementations described herein may also use machine learning to aid in identifying or smoothing the final contour of a vessel or other structure of interest. The machine learning processing (e.g., within post processing unit 240) may receive image data and generate probability information for each particular portion of the image (e.g., pixel) to determine the probability that the particular portion is within the target vessel. Post processing unit 240 may further refine the probability information using additional information, such as the gender or age of the patient, the particular target organ, etc.

The foregoing description of exemplary implementations provides illustration and description, but is not intended to be exhaustive or to limit the embodiments to the precise form disclosed. Modifications and variations are possible in light of the above teachings or may be acquired from practice of the embodiments.

For example, features have been described above with respect to identifying a target of interest, such as a patient's abdominal aorta, a lumen within the abdominal aorta and a thrombus/thrombus region, and estimating the size of the target (e.g., the aorta, lumen and/or the thrombus). In other implementations, other vessels, organs or structures may be identified, and sizes or other parameters associated with the vessels, organs or structures may be estimated. For example, the processing described herein may be used to identify and display a bladder, prostate gland, a kidney, a uterus, ovaries, a heart, etc., as well as particular features associated with these targets, such as volume-related measurements.

Further, while series of acts have been described with respect to FIG. 6, the order of the acts may be different in other implementations. Moreover, non-dependent acts may be implemented in parallel.

It will be apparent that various features described above may be implemented in many different forms of software, firmware, and hardware in the implementations illustrated in the figures. The actual software code or specialized control hardware used to implement the various features is not limiting. Thus, the operation and behavior of the features were described without reference to the specific software code—it being understood that one of ordinary skill in the art would be able to design software and control hardware to implement the various features based on the description herein.

Further, certain portions of the invention may be implemented as "logic" that performs one or more functions. This logic may include hardware, such as one or more processors, microprocessor, application specific integrated circuits, field programmable gate arrays or other processing logic, software, or a combination of hardware and software.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

What is claimed is:

1. A system, comprising:
   a probe configured to:
      transmit ultrasound signals directed to a target blood vessel, and
      receive echo information associated with the transmitted ultrasound signals; and
   at least one processing device configured to:
      process the received echo information and generate an ultrasound image of the blood vessel,
      identify a seed position within the blood vessel based on the ultrasound image,
      generate, using the seed position, an estimated contour for a lumen of the blood vessel based on pixel intensity values associated with the ultrasound image;
      generate an estimated contour for the blood vessel based on the pixel intensity values associated with the ultrasound image,
      determine whether a thrombus exists within the blood vessel based on at least one of a distance between a boundary of the lumen and a boundary of the blood vessel, or at least one of a size or area of the lumen compared to at least one of a size or area of the blood vessel;
      output image information illustrating the estimated contour of the lumen, and
      output image information illustrating the estimated contour of the blood vessel.

2. The system of claim 1, wherein the blood vessel is the abdominal aorta and wherein the at least one processing device is further configured to:
   determine that the thrombus exists when the at least one of the size or area of the lumen is less than a predetermined percentage of the at least one of the size or area of the abdominal aorta.

3. The system of claim 2, wherein the at least one processing device is further configured to:
   output an indicator or icon representing a location of the thrombus.

4. The system of claim 3, further comprising:
   a display configured to:
      receive the image information illustrating the estimated contours of the lumen and the abdominal aorta,
      display the image information illustrating the estimated contours of the lumen and the abdominal aorta,
      display the diameter of the lumen, and
      display the diameter of the abdominal aorta.

5. The system of claim 1, wherein when identifying a seed position within the blood vessel, the at least one processing device is further configured to:
   estimate a center position within the lumen of the blood vessel based on the pixel intensity values associated with the ultrasound image, and
   use the estimated center position as the seed position.

6. The system of claim 1, wherein when generating the estimated contour for the lumen, the at least one processing device is further configured to:
   extend a plurality of radial lines from the seed position to a location beyond an expected boundary of the lumen,
   determine cost values at candidate nodes on each of the plurality of radial lines, and
   determine a contour of the lumen based on a cost function analysis of paths through the candidate nodes.

7. The system of claim 6, wherein when determining cost values and a contour of the lumen, the at least one processing device is further configured to:
   determine first cost values based on pixel values at or around the candidate nodes,
   determine second cost values associated with local smoothness of the contour based on the candidate node positions, and
   select a contour of the lumen that minimizes a global weighted sum of the first and second cost values.

8. The system of claim 1, wherein when generating the estimated contour for the blood vessel, the at least one processing device is further configured to:
   extend a plurality of radial lines from the contour of the lumen to a location beyond an expected boundary of the blood vessel,
   determine cost values at candidate nodes on each of the plurality of radial lines, and
   determine a contour of the blood vessel based on a cost function analysis of paths through the candidate nodes.

9. The system of claim 8, wherein when determining cost values and a contour of the blood vessel, the at least one processing device is further configured to:
   determine first cost values based on pixel values at or around the candidate nodes,
   determine second cost values associated with local smoothness of the contour of the lumen based on the candidate node positions, and
   select a contour of the blood vessel that minimizes a global weighted sum of the first and second cost values.

10. The system of claim 1, wherein when determining whether a thrombus exists within the blood vessel, the at least one processing device is configured to:
    determine at least one of a size or area of the lumen,
    determine at least one of a size or area of the blood vessel, and
    determine that a thrombus exists based on the size or area of the lumen and the size or area of the blood vessel.

11. The system of claim 1, wherein the probe is further configured to:
    generate three-dimensional image information of the target blood vessel based on the received echo information.

12. A method, comprising:
transmitting ultrasound signals directed to a target blood vessel;
receiving echo information associated with the transmitted ultrasound signals;
processing the received echo information and generating an ultrasound image of the blood vessel;
identifying a seed position within the blood vessel based on the ultrasound image;
generating, using the seed position, a contour of a lumen of the blood vessel based on pixel intensity values associated with the ultrasound image;
generating a contour for the blood vessel based on the pixel intensity values associated with ultrasound image;
determining whether a thrombus exists within the blood vessel based on at least one of a distance between a boundary of the lumen and a boundary of the blood vessel, or at least one of a size or area of the lumen compared to at least one of a size or area of the blood vessel; and
outputting image information illustrating the estimated contour of the blood vessel.

13. The method of claim 12, wherein the blood vessel is the abdominal aorta, the method further comprising:
determining at least one of a diameter or an area of the abdominal aorta based on the estimated contour for the abdominal aorta.

14. The method of claim 13, further comprising:
outputting image information illustrating the estimated contour of the lumen.

15. The method of claim 14, further comprising:
displaying the image information illustrating the contours of the lumen and the abdominal aorta; and
displaying the at least one of the diameter or the area of the abdominal aorta.

16. The method of claim 12, wherein identifying a seed position within the blood vessel comprises:
estimating a center position within the lumen of the blood vessel based on the pixel intensity values, and
using the estimated center position as the seed position.

17. The method of claim 12, wherein generating the contour of the lumen comprises:
extending a plurality of radial lines from the seed position to a location beyond an expected boundary of the lumen,
determining cost values at candidate nodes on each of the plurality of radial lines, and
determining a contour of the lumen based on a cost function analysis of paths through the candidate nodes.

18. The method of claim 17, wherein when generating the contour of the blood vessel comprises:
extending a plurality of radial lines from the contour of the lumen to a location beyond an expected boundary of the blood vessel,
determining cost values at candidate nodes on each of the plurality of radial lines, and
determining a contour of the blood vessel based on a cost function analysis of paths through the candidate nodes.

19. A non-transitory computer-readable medium having stored thereon sequences of instructions which, when executed by at least one processor, cause the at least one processor to:
receive echo information associated with ultrasound signals transmitted via an ultrasound scanner;
process the received echo information and generate an ultrasound image of a blood vessel;
identify a seed position within the blood vessel based on the ultrasound image;
generate, using the seed position, a contour for a lumen of the blood vessel based on pixel intensity values associated with the ultrasound image;
generate a contour for the blood vessel based on the pixel intensity values associated with the ultrasound image;
determine whether a thrombus exists within the blood vessel based on the contour for the lumen and the contour for the blood vessel;
output image information illustrating the contour of the lumen; and
output image information illustrating the contour of the blood vessel.

20. The non-transitory computer-readable medium of claim 19, wherein the blood vessel comprises the abdominal aorta.

* * * * *